United States Patent
Yamada et al.

(10) Patent No.: US 9,020,586 B2
(45) Date of Patent: Apr. 28, 2015

(54) BRAIN ACTIVITY MEASURING APPARATUS, BRAIN ACTIVITY MEASURING METHOD, BRAIN ACTIVITY DEDUCING APPARATUS, BRAIN ACTIVITY DEDUCING METHOD, AND BRAIN-MACHINE INTERFACE APPARATUS

(75) Inventors: Kentaro Yamada, Wako (JP); Yukiyasu Kamitani, Kyoto (JP)

(73) Assignees: Honda Motor Co., Ltd., Tokyo (JP); Advanced Telecommunications Research Institute International, Kyoto (JP)

( * ) Notice: Subject to any disclaimer, the term of this patent is extended or adjusted under 35 U.S.C. 154(b) by 386 days.

(21) Appl. No.: 13/469,589

(22) Filed: May 11, 2012

(65) Prior Publication Data

US 2012/0289854 A1   Nov. 15, 2012

(30) Foreign Application Priority Data

May 13, 2011   (JP) ................ P2011-108749

(51) Int. Cl.
| | | |
|---|---|---|
| *A61B 5/04* | (2006.01) | |
| *G01R 33/48* | (2006.01) | |
| *A61B 5/0484* | (2006.01) | |
| *A61B 5/055* | (2006.01) | |
| *G06F 3/01* | (2006.01) | |

(52) U.S. Cl.
CPC ........ *G01R 33/4806* (2013.01); *A61B 5/04842* (2013.01); *A61B 5/055* (2013.01); *G06F 3/015* (2013.01); *A61B 2576/026* (2013.01)

(58) Field of Classification Search
CPC ............ A61B 5/0476; A61B 5/04012; A61B 5/0482; A61B 5/0484; A61B 5/04842; A61B 5/04845
USPC ......................................... 600/410, 544, 545
See application file for complete search history.

(56) References Cited

U.S. PATENT DOCUMENTS

| | | | | |
|---|---|---|---|---|
| 2007/0032738 | A1* | 2/2007 | Flaherty et al. ............... | 600/545 |
| 2008/0249430 | A1* | 10/2008 | John et al. ...................... | 600/544 |
| 2009/0221928 | A1* | 9/2009 | Einav et al. ................... | 600/544 |
| 2009/0270753 | A1* | 10/2009 | Adachi et al. ................. | 600/544 |
| 2011/0257517 | A1* | 10/2011 | Guttag et al. ................. | 600/425 |

FOREIGN PATENT DOCUMENTS

JP   2008-229238 A   10/2008

* cited by examiner

*Primary Examiner* — Etsub Berhanu
(74) *Attorney, Agent, or Firm* — Squire Patton Boggs (US) LLP

(57) ABSTRACT

What is provides is a brain activity deducing apparatus, a brain activity deducing method, a brain activity measuring apparatus, a brain activity measuring method, and a brain-machine interface device, capable of deducing a brain activity signal of a source subject. The information presentation device presents perceptible information to the first subject. The brain activity measurement device acquires a brain activity signal representing a brain activity of the first subject. The individual conversion device deduces a brain activity signal of the second subject from the acquired brain activity signal based on the individual conversion information, which correlates the brain activity signal of the first subject and the brain activity signal of the second subject.

10 Claims, 13 Drawing Sheets ep1 it1 it2 it3 it4 ip1 ip2 ip3 ip4 ip5 ip1 mi1 mpi1 mi2 mpi2

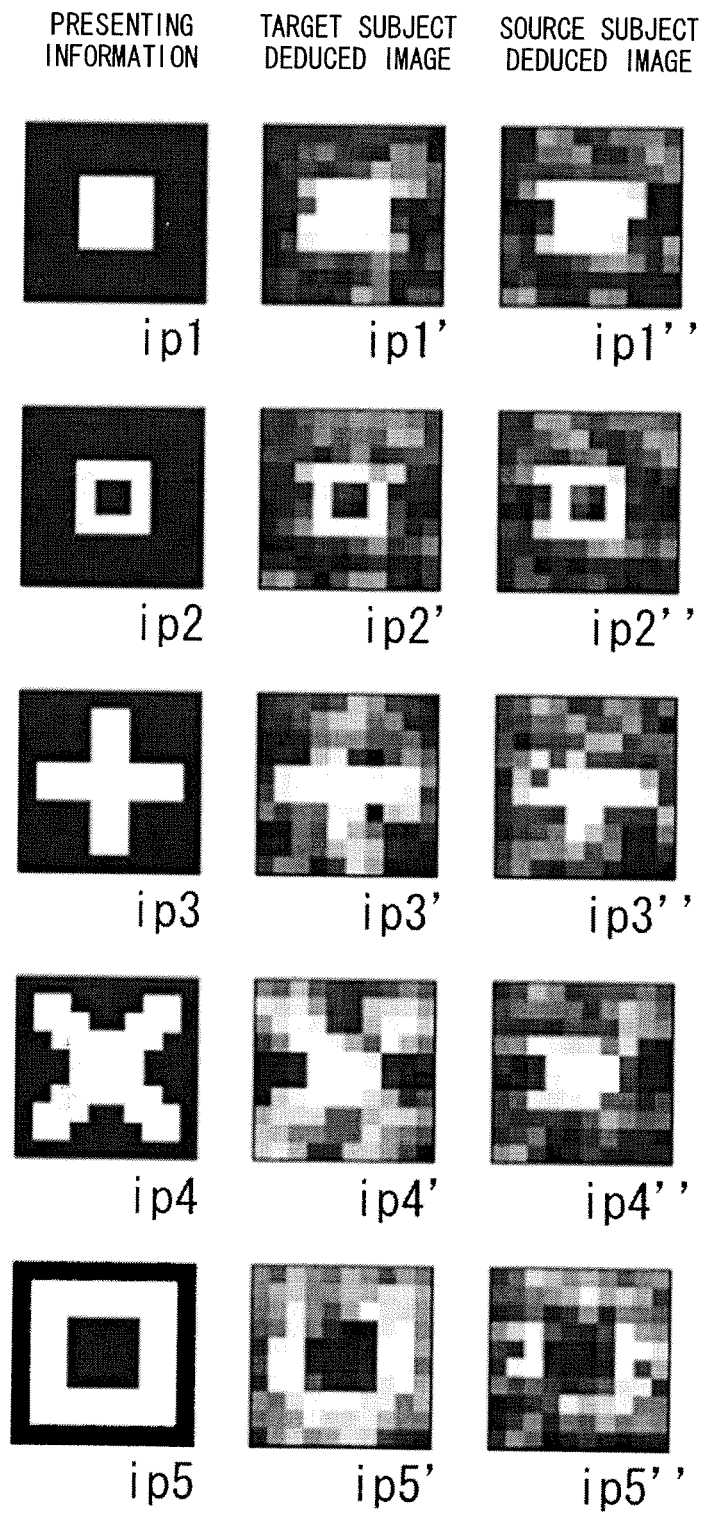

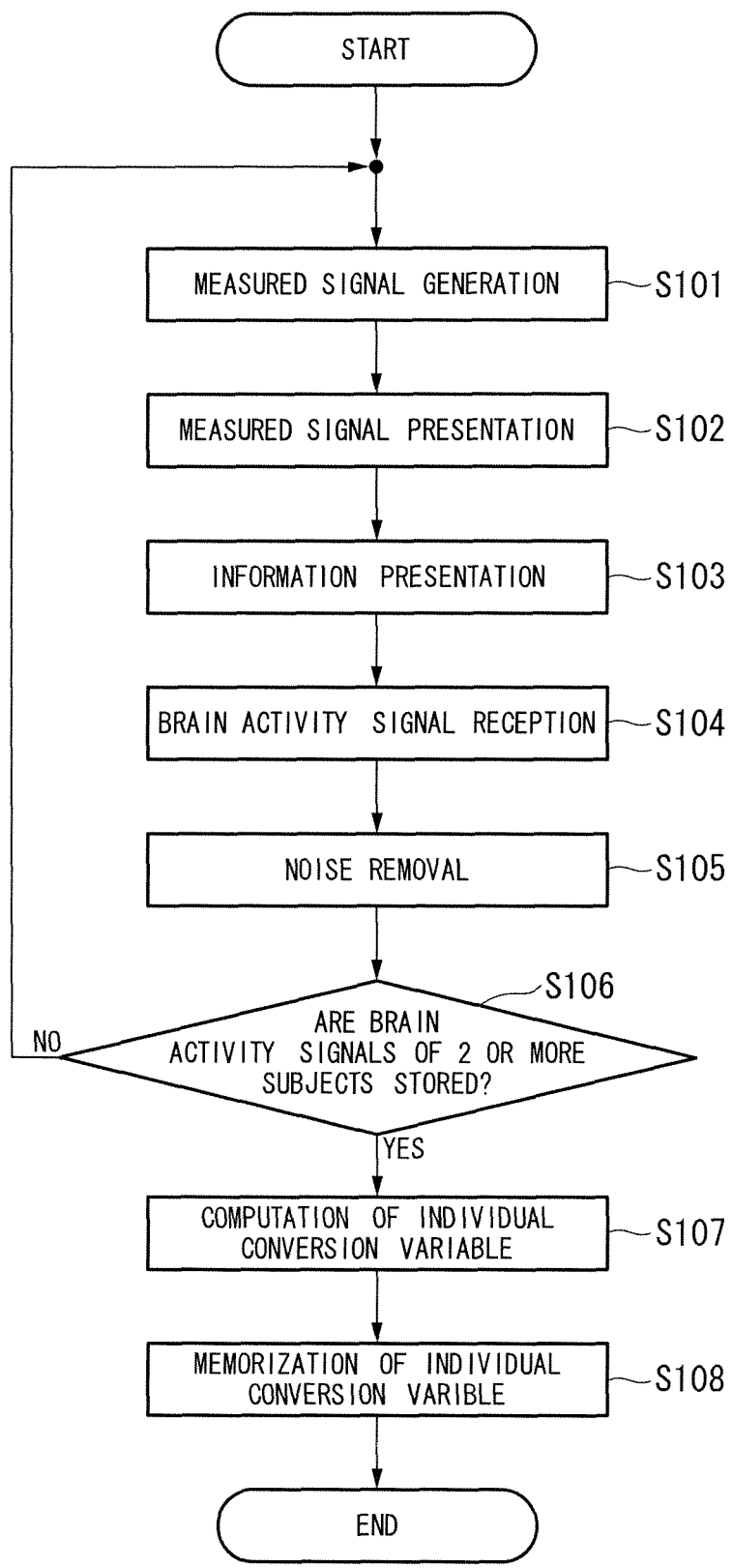

FIG. 13

|  |  | SOURCE SUBJECTS | | |
|---|---|---|---|---|
|  |  | SUBJECT 1 | SUBJECT 2 | SUBJECT 3 |
| TARGET SUBJECTS | SUBJECT 1 | — | 0.54 (±0.12) | 0.49 (±0.14) |
|  | SUBJECT 2 | 0.42 (±0.15) | — | 0.31 (±0.18) |
|  | SUBJECT 3 | 0.19 (±0.23) | 0.15 (±0.21) | — |

FIG. 14

|  |  | SOURCE SUBJECTS | | |
|---|---|---|---|---|
|  |  | SUBJECT 1 | SUBJECT 2 | SUBJECT 3 |
| TARGET SUBJECTS | SUBJECT 1 | — | 87 | 86 |
|  | SUBJECT 2 | 84 | — | 82 |
|  | SUBJECT 3 | 49 | 62 | — |

FIG. 15

|  |  | SOURCE SUBJECTS | | |
|---|---|---|---|---|
|  |  | SUBJECT 1 | SUBJECT 2 | SUBJECT 3 |
| TARGET SUBJECTS | SUBJECT 1 | - | 0.72 (±0.12) | 0.60 (±0.14) |
|  | SUBJECT 2 | 0.74 (±0.08) | - | 0.57 (±0.13) |
|  | SUBJECT 3 | 0.67 (±0.13) | 0.61 (±0.15) | - |

US 9,020,586 B2

BRAIN ACTIVITY MEASURING APPARATUS, BRAIN ACTIVITY MEASURING METHOD, BRAIN ACTIVITY DEDUCING APPARATUS, BRAIN ACTIVITY DEDUCING METHOD, AND BRAIN-MACHINE INTERFACE APPARATUS

BACKGROUND OF THE INVENTION

1. Field of the Invention

The present invention relates a brain activity measuring apparatus, a brain activity measuring method, a brain activity deducing apparatus, a brain activity deducing method, and a brain-machine interface apparatus Priority is claimed on Japanese Patent Application No. 2011-108749, filed May 13, 2011, the content of which is incorporated herein by reference.

2. Description of Related Art

A human brain, which is responsible for a human behavior, processes information. In order to deduce the information, it has been attempted to establish a model correlating a brain activity and a signal generated by the activity. For example, a technique, in which a signal generated by a human brain activity is measured and a brain activity is analyzed based on the measured signal, has been proposed.

For example, a technique for analyzing a brain activity model has been proposed (see Japanese Unexamined Patent Application, First Publication No. 2008-229238). In this technique, a signal strength distribution formed at a circumferential part of a head is measured through time. Then, an amplitude distribution of each current element in a cerebral nerve model is re-constructed based on the measured time-series data. Then, the cerebral nerve model is configured based on the time-series data of each current element. Then, a causal connection of the brain activity model is extrapolated based on the time-series data of each current element.

SUMMARY OF THE INVENTION

In the conventional method disclosed in Japanese Unexamined Patent Application, First Publication No. 2008-229238, it is necessary to acquire enormous volume of time-series data in order to configure the cerebral nerve model. The data needed to be acquired are image information obtained by MRI (Magnetic Resonance Imaging) or brain wave (Electroen cephalogram: EEG) signals for example. In order to configure the cerebral nerve model, a subject (a person subjected to a measurement) has to be constrained for a long period of time under a large-scale measurement device. Furthermore, the measurement has to be done on a case-by-base basis, since the measured brain activity signals are different in each subject even if the same information was presented to all subjects.

The present invention is made under the above-described circumstance. The present invention provides a brain activity measuring apparatus, a brain activity measuring method, a brain activity deducing apparatus, a brain activity deducing method, a brain-machine interface device, capable of deducing the brain activity signal of the target subject.

In order to solve the above-mentioned problem, the present invention has aspects shown below.

(1) A brain activity measuring apparatus including: an information presentation device that presents perceptible information to a subject; a brain activity measurement device that acquires a brain activity signal representing a brain activity of the subject; and an individual conversion information computation device that computes an individual conversion information, which correlates the brain activity signal of a first subject and the brain activity signal of a second subject.

(2) The brain activity measuring apparatus described in (1) above, wherein the brain activity measurement device resolves the acquired brain activity signal into element signals; element signal intensities of the brain activity signal are information indicating brain activity levels per voxel in a cephalic part of the first subject or the second subject; the individual conversion information computation device computes, as the individual conversion information, correlation coefficients each of which correlates an element signal of an i-th voxel of the first subject and an element signal of a j-th voxel of the second subject by using the hierarchical Baysian estimation.

(3) The brain activity measuring apparatus described in (2) above, wherein the individual conversion information computation device sets a weight corresponding to one of the correlation coefficients to 0 during computing the individual conversion information by an iterative operation for the hierarchical Baysian estimation, in a case where correlation between the element signal of the i-th voxel of the first subject and the element signal of the j-th voxel of the second subject is determined to be low based on a predetermined threshold value.

(4) The brain activity measuring apparatus described in (3) above, further including an individual conversion information memory device that stores the individual conversion information of every pair of the first subject and the second subject.

(5) The brain activity measuring apparatus described (4) above, further including an individual conversion device that deduces the brain activity of the second subject from the brain activity of the first subject measured with the brain activity measurement device based on the correlation coefficient stored in the individual conversion information memory device.

(6) A brain activity measuring method in which a brain activity of a subject is measured with a brain activity measuring apparatus including: a first step of presenting, by the brain activity measuring apparatus, perceptible information to a subject; a second step of acquiring, by the brain activity measuring apparatus, a brain activity signal representing a brain activity of the subject; and a computing step of computing, by the brain activity measuring apparatus, an individual conversion information, which correlates the brain activity signal of a first subject and the brain activity signal of a second subject.

(7) A brain activity deducing apparatus including: an information presentation device that presents perceptible information to a first subject; a brain activity measurement device that acquires a brain activity signal representing a brain activity of the first subject; and an individual conversion device that deduces a brain activity signal of a second subject from the acquired brain activity signal based on an individual conversion information, which correlates the brain activity signal of a first subject and the brain activity signal of the second subject.

(8) The brain activity deducing apparatus described in (7) above, further including a reconstructed model generation device generating a reconstructed model of a presented information, wherein the reconstructed model generation device outputs an image signal, which represents an 1-frame image corresponding to the presented information, from the deduced brain activity signal of the second subject as a linear combination of respective products of local basal images and deduced contrast values.

(9) A brain activity deducing method in which a brain activity of a subject is deduced with a brain activity deducing apparatus including the steps of: presenting perceptible information to a first subject with the brain activity deducing apparatus; acquiring a brain activity signal representing a brain activity of the first subject with the brain activity deducing apparatus; and deducing a brain activity signal of a second subject from the acquired brain activity signal based on an individual conversion information with the brain activity deducing apparatus, wherein the brain activity deducing device includes an individual conversion information memory device that stores the individual conversion information, which correlates the brain activity signal of the first subject and the brain activity signal of the second subject.

(10) A brain-machine interface device including: an information presentation device that presents perceptible information to a first subject; a brain activity measurement device that acquires a brain activity signal representing a brain activity of the first subject; an individual conversion device that deduces a brain activity signal of a second subject from the acquired brain activity signal based on an individual conversion information, which correlates the brain activity signal of the first subject and the brain activity signal of the second subject; and a control signal conversion device that converts the brain activity signal of the second subject deduced with the individual conversion device to a control signal controlling an external device.

According to the aspect of the present invention described in (1) above, a brain activity measuring apparatus capable of obtaining the individual conversion information for deducing the brain activity signal of the target subject is provided.

Also, according to the aspect of the present invention described in (6) above, a brain activity measuring method capable of obtaining the individual conversion information for deducing the brain activity signal of the target subject is provided.

Also, according to the aspect of the present invention described in (7) above, a brain activity deducing apparatus capable of deducing the brain activity signal of the target subject is provided.

Also, according to the aspect of the present invention described in (9) above, a brain activity deducing method capable of deducing the brain activity signal of the target subject is provided.

Also, according to the aspect of the present invention described in (10) above, a brain-machine interface device capable of controlling an external device by the deduced brain activity signal of the target subject is provided.

BRIEF DESCRIPTION OF THE DRAWINGS

FIG. 9 is a figure showing examples of presented information reconstructed by the reconstructed model generation device related to an embodiment of the present invention.

FIG. 10 is a flowchart showing an example of the brain activity measuring process performed by the brain activity deducing apparatus related to an embodiment of the present invention.

FIG. 13 is a table showing an example indicating the correlation between the brain activity signals related to an embodiment of the present invention.

FIG. 14 is a table showing an example indicating the percentage of correct answers of the presented information related to an embodiment of the present invention.

FIG. 15 is a table showing an example indicating the correlation between the presented information related to an embodiment of the present invention.

DETAILED DESCRIPTION OF THE INVENTION

First, a brief overview of the present invention is explained with reference to drawings.

Figure 1:
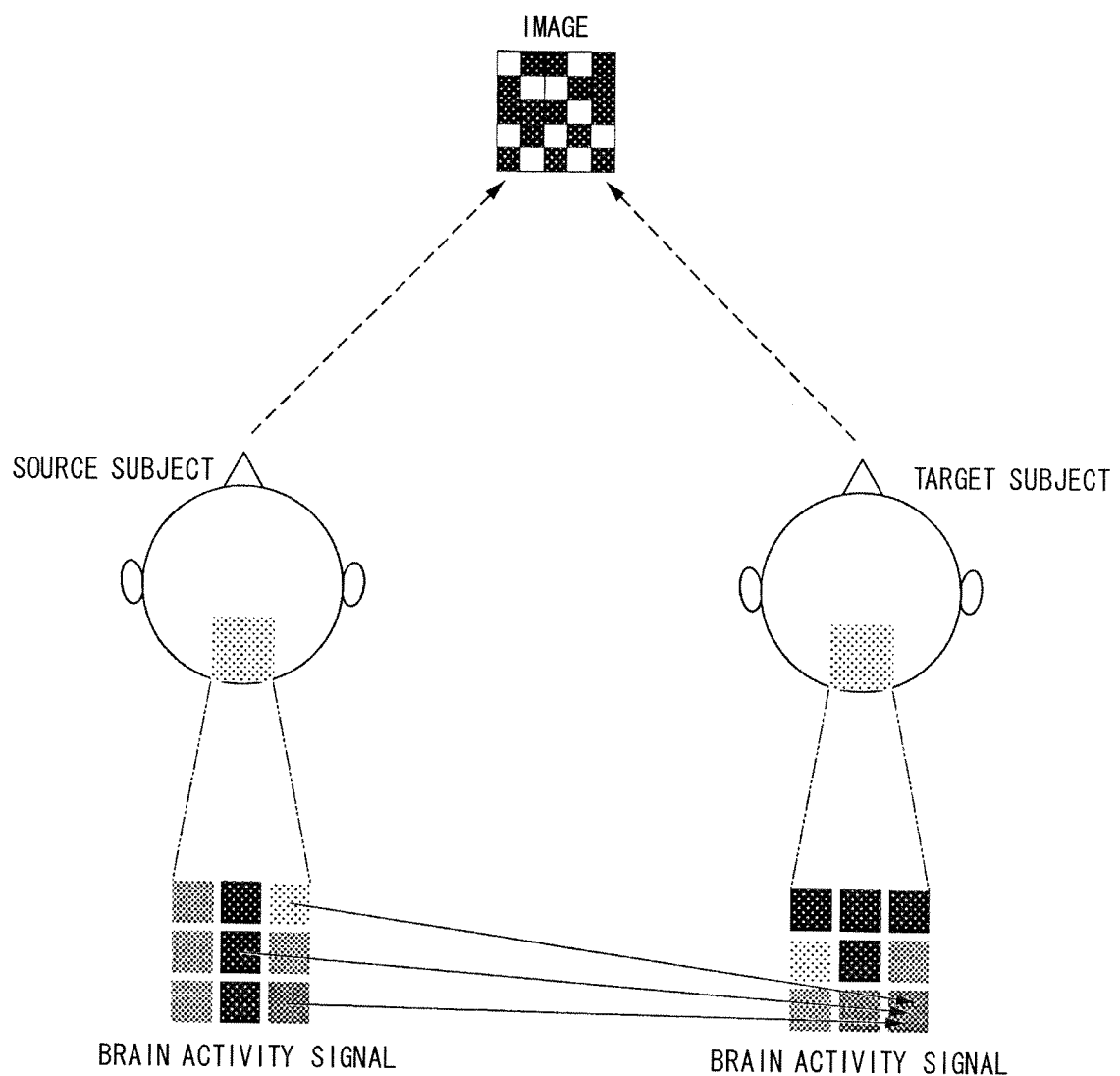
FIG. 1 is a conceptual diagram showing an brief overview of the brain activity measuring process related to an aspect of the present invention.

FIG. 1 is a conceptual diagram showing an brief overview of the brain activity measuring process related to an aspect of the present invention.

In FIG. 1, brain activity signals of two subjects are measured individually. Then, an individual conversion information representing the correlation between the brain activity signal of a first subject and the brain activity signal of a second subject is computed based on the measured brain activity signals. The individual conversion information is an information used for generating the brain activity signal of the second subject based on the brain signal of the first subject. The first subject, who the conversion source brain activity signal was measured from, is called as a source subject. The second subject, who the conversion target brain activity signal was measured from, is called as a target subject. The second subject whose brain activity signal is intended to be computed is also called as a target subject.

In FIG. 1, the same image is presented to both the source and target subjects. Then, the brain activity signals measured in each subject are acquired. At this time, the brains of each subject process information related to the viewed image, and the brain activity signals representing the action are generated. The brain activity signals are usually presented as a vector including signal values of elements as element signals. In FIG. 1, the signal intensity of the each element signal is indicated by a grayscale.

In FIG. 1, it is shown that the measured brain activity signals are different between subjects who are presented the same image. The arrows drawn from each element signal of the brain activity signal obtained from the source subject to the single element signal of the target subject indicate that the individual conversion signal is computed based on the single element signal of the target subject and the each element signal of the brain activity signals obtained from the source subject.

Figure 2:
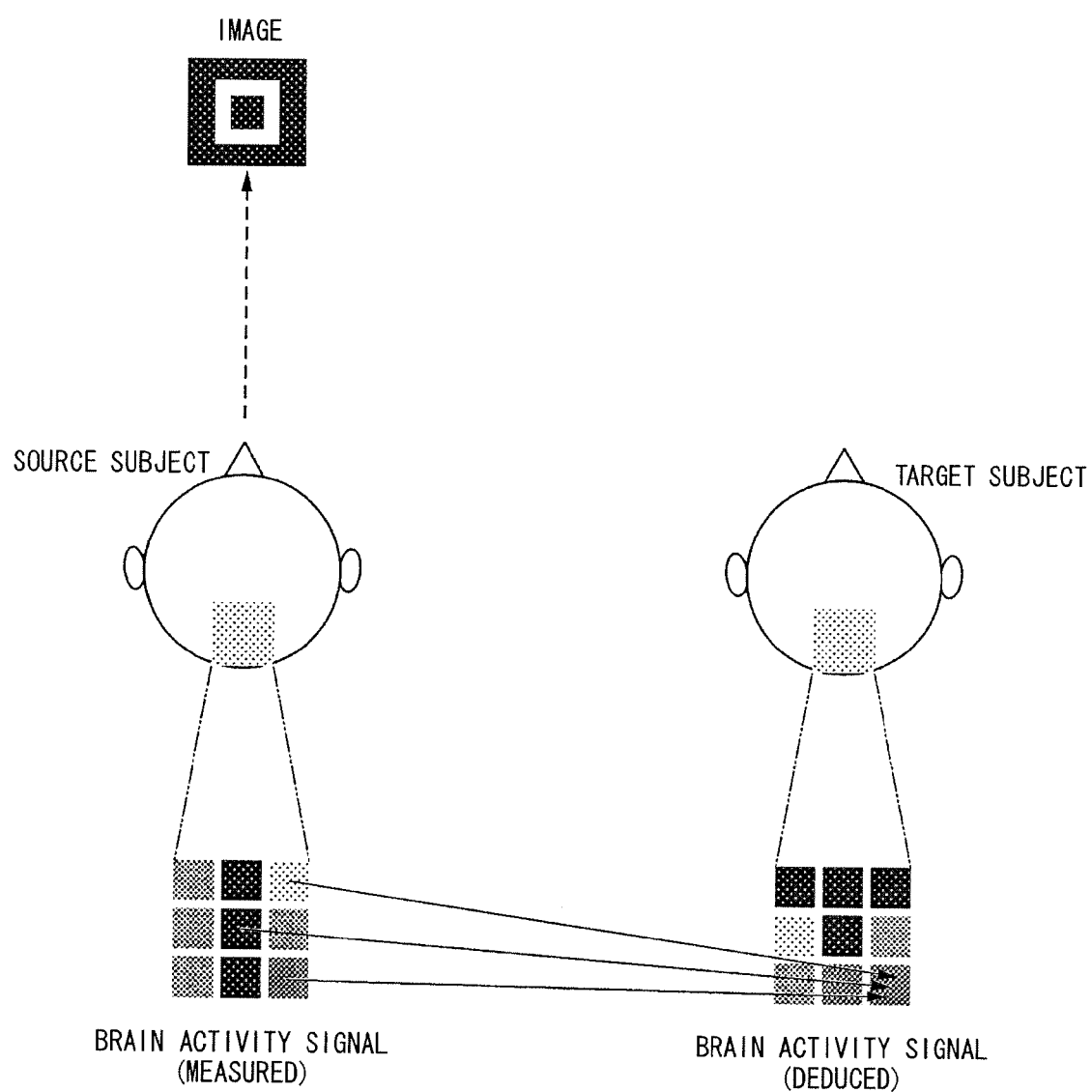
FIG. 2 is a conceptual diagram showing an brief overview of the brain activity deducing process related to an aspect of the present invention.

FIG. 2 is a conceptual diagram showing an brief overview of the brain activity deducing process related to an aspect of the present invention.

In FIG. 2, the image is presented only to the source subject, and brain activity signals of the source subject is measured. Then, the brain activity signal of the target subject is deduced based on the measured brain activity signal.

In FIG. 2, the measured brain activity signals obtained from the source subject and deduced brain activity signals of the target subject are shown. The arrows drawn from each element signal of the brain activity signal obtained from the source subject to the single element signal of the target subject indicate that the single element signal of the target subject is deduced based on the each element signal of the brain activity signals obtained from the source subject.

Next, embodiments of the present invention are explained.

Figure 3:
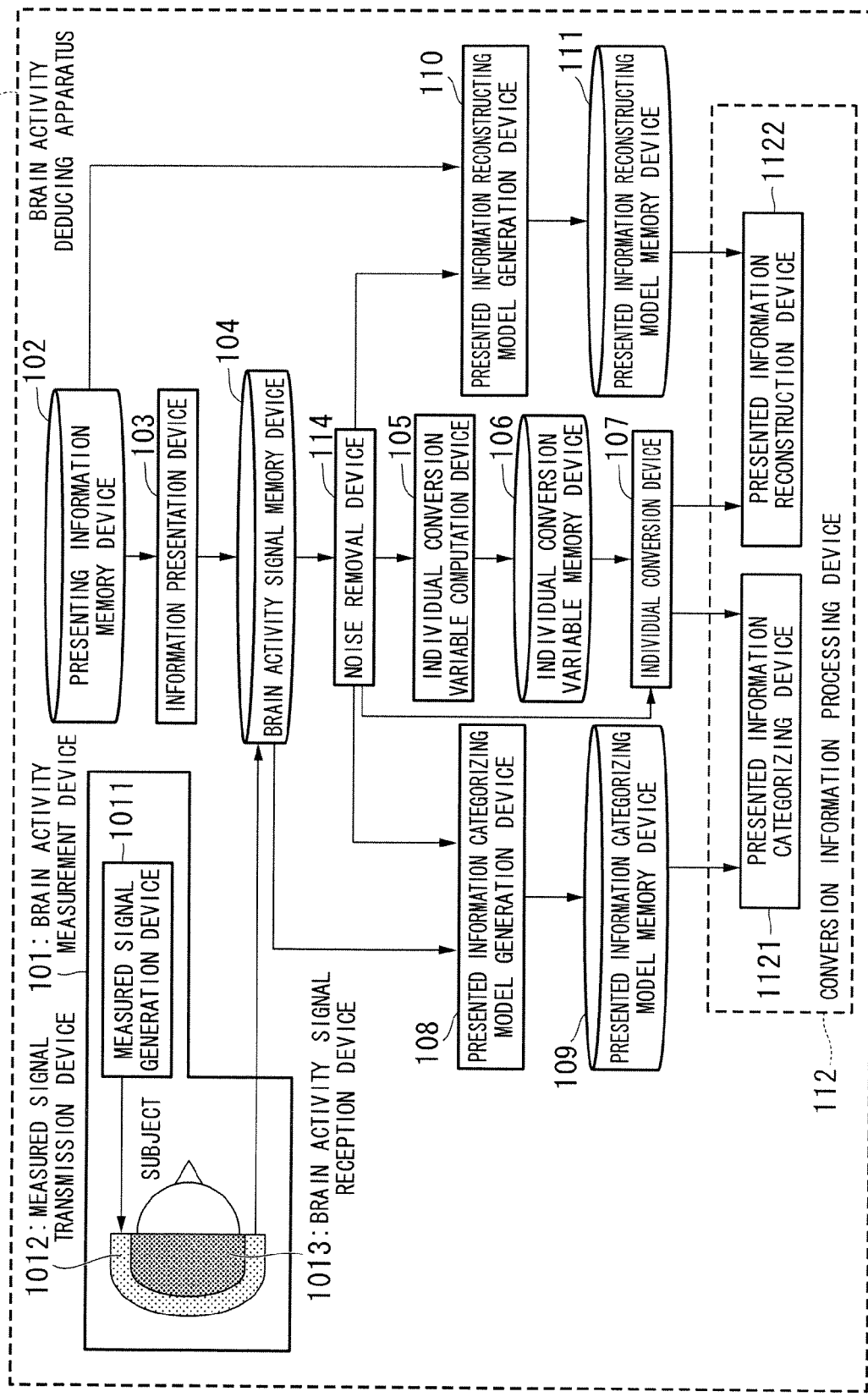
FIG. 3 is a schematic diagram showing a configuration of a brain activity deducing apparatus related to an aspect of the present invention.

FIG. 3 is a schematic diagram showing a configuration of a brain activity deducing apparatus 1 related to an aspect of the present invention.

The brain activity deducing apparatus 1 includes: a brain activity measurement device 101; a presenting information memory device 102; an information presentation device 103; a brain activity signal memory device 104; an individual conversion variable computation device 105; an individual conversion variable memory device 106; an individual conversion device 107; a presented information categorizing model generation device 108; a presented information categorizing model memory device 109; a presented information reconstructing model generation device 110; a presented information reconstructing model memory device 111; a conversion information processing device 112; and a noise removal device 114.

The brain activity measurement device 101 measures the brain activity signals generated when the brain of the subject to be measured performs a task. The measured signals are stored by the brain activity signal memory device 104.

The brain activity signals measured by the brain activity measurement device 101 are signals obtained by EPI (Echo Planar Imaging) method for example. The EPI method is a kind of MRI (Magnetic Resonance Imaging) method. The element signal in the EPI signal is defined for each voxel, which is an unit of a space forming a three-dimensional space to be measured. A number of voxels obtained in a single measurement, is 64 voxels in the side direction, 64 voxels in the longitudinal direction, and 64 voxels in the height direction for example. The widths of the voxels are 3 mm each in the side, longitudinal, and height directions.

In order to acquire the EPI signals, the brain activity measurement device 101 includes: a measured signal generation device 1011; a measured signal transmission device 1012; and a brain activity signal reception device 1013, for example.

The measured signal generation device 1011 generates a measurement signal representing a magnetic field signal used for measuring the brain activity signal. Then, the measured signal generation device 1011 outputs the generated measurement signal to the measured signal transmission device 1012. The measured signal generation device 1011 generates the measurement signal as a pulse wave with an extremely short duration (for example, 2 ms), for example.

The measured signal transmission device 1012 generates magnetic field based on the measurement signal fed from the measured signal generation device 1011. Then, the measured signal transmission device 1012 transmits the generated magnetic field to the cephalic part of the subject to be measured. In a case where the fed measurement signal is a pulse wave, the measured signal transmission device 1012 generates a pulse magnetic field and transmits the generated pulse magnetic field to the subject to be measured. Simultaneously, the measured signal transmission device 1012 transmits a gradient field having different intensities depending on the measurement locations to the cephalic part of the subject to be measured.

The brain activity signal reception device 1013 receives the brain activity signals representing activities for each part on the cephalic part of the subject to be measured. The brain activity signal reception device 1013 detects signals generated by the relaxation phenomenon as the brain activity signals. The relaxation phenomenon is a phenomenon in which a magnetized molecule in the body of the subject to be measured is returned to the steady state after stopping application of the magnetic field. The brain activity signal reception device 1013 resolves the detected signal into element signals for each location of the measured space (voxel) based on the intensity of the gradient field. Then, the brain activity signal reception device 1013 generates the brain activity signal (for example, an EPI signal). The brain activity signal reception device 1013 performs the Fourier Transformation in order to resolve the detected signal into the element signals, for example. The intensity of the element signal is proportional to the amount of hemoglobin, which is the molecule inside the space to be measured, in the blood stream. Therefore, it represents the extent of the brain activity in the corresponding part (voxel).

The brain activity signal reception device 1013 transmits the generated brain activity signal to the brain activity signal memory device 104.

Here, an example of the brain activity signal obtained by the brain activity signal reception device 1013 is shown.

Figure 4:
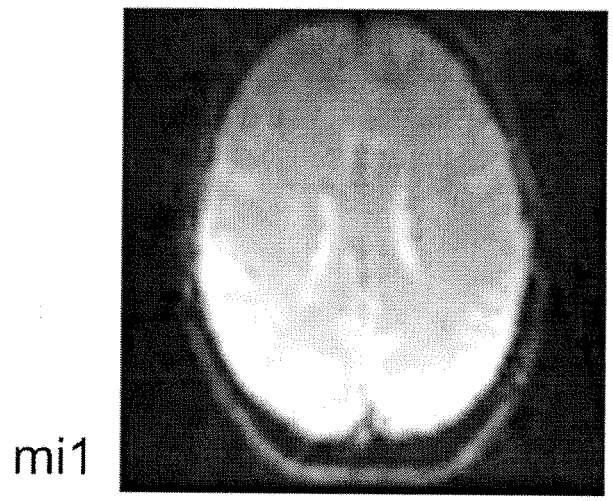
FIG. 4 is a figure showing an example of the brain activity signal related to an embodiment of the present invention.

FIG. 4 is a figure showing an example of the brain activity signal related to an embodiment of the present invention.

In FIG. 4, the image mi1 is an image showing the element signals representing the brain activity as a pixel value in a cross-section view of the cephalic part of the subject to be measured. The grey scale value of the image mi1 indicates the signal value of the element signals, and the brighter the spot, the higher the value. In the image mi1, the upper part is the part in the vicinity of the frontal cortex.

Explanation of FIG. 3 is resumed below. The brain activity measurement device 101 can obtain not only the above-described EPI signals but the brain wave as the brain activity signals. In that case, the brain activity measurement device 101 includes multiple monitoring electrodes (for example, 18 electrodes) placed at the cephalic part of the subject to be measured in order to acquire the electrical potential as the element signals constituting the brain wave.

An example of the locations that the monitoring electrodes to be placed is explained below.

Figure 5:
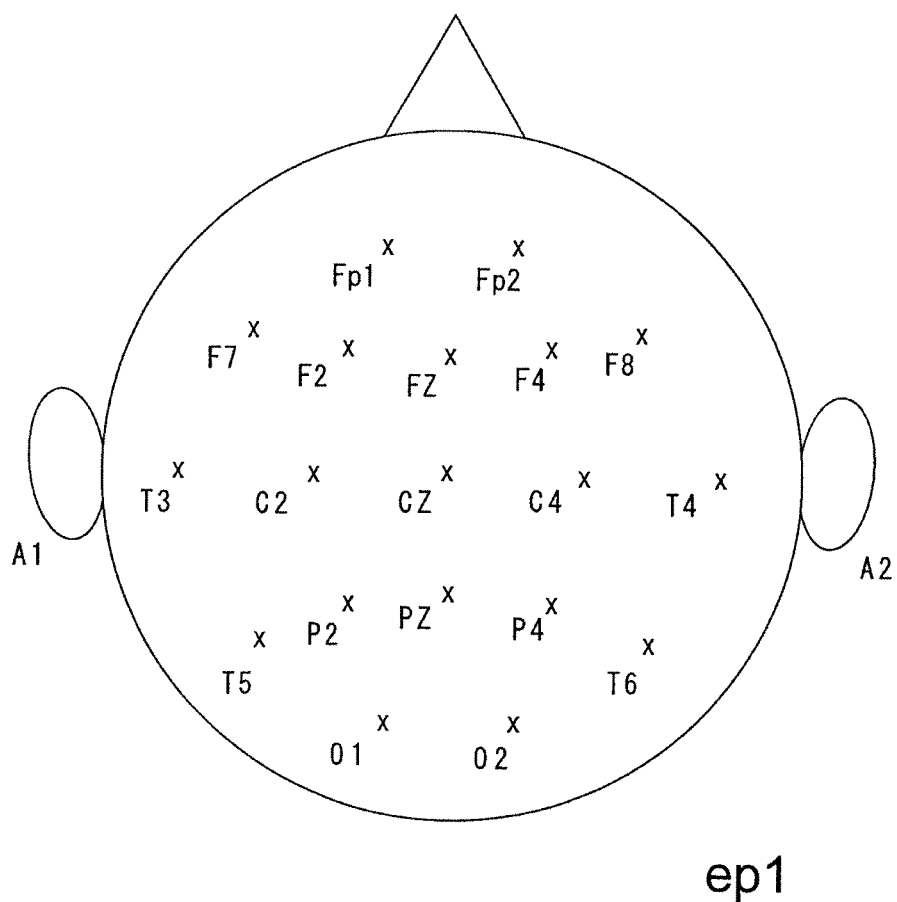
FIG. 5 is a conceptual diagram showing an example of locations, which the monitoring electrodes are placed, in an embodiment of the present invention.
Figure 6A:
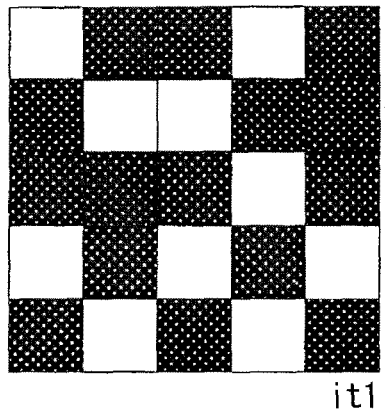
FIG. 6A to FIG. 6D are figures showing examples of the presented information related to an embodiment of the present invention.
Figure 6B:
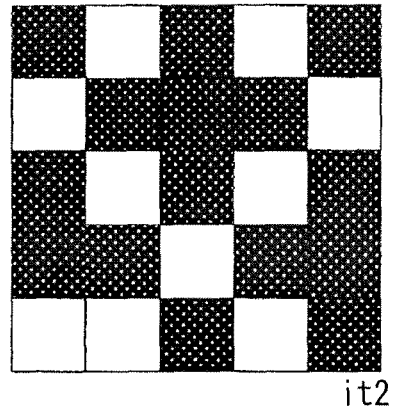
Figure 6C:
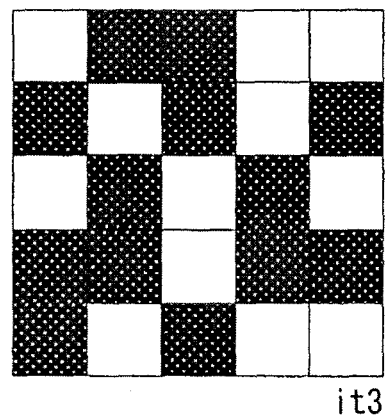
Figure 6D:
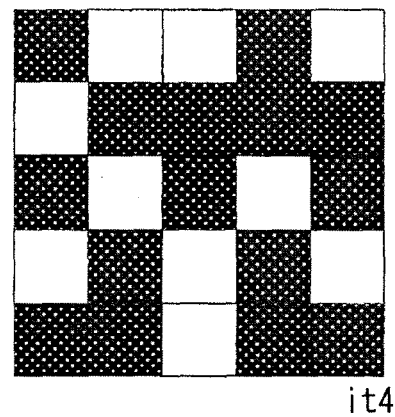
Figure 7A:
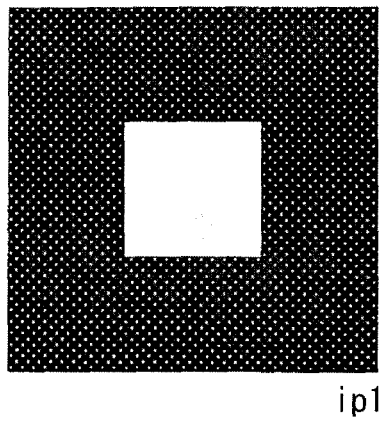
FIG. 7A to FIG. 7E are figures showing other examples of the presented information related to an embodiment of the present invention.
Figure 7B:
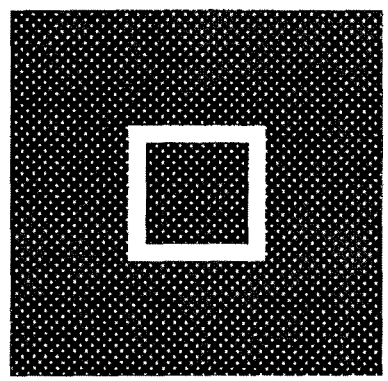
Figure 7C:
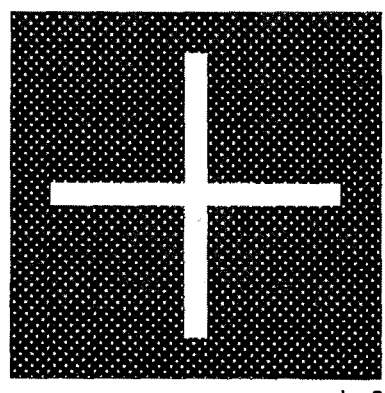
Figure 7D:
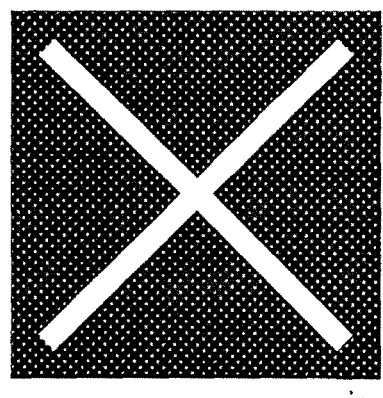
Figure 7E:
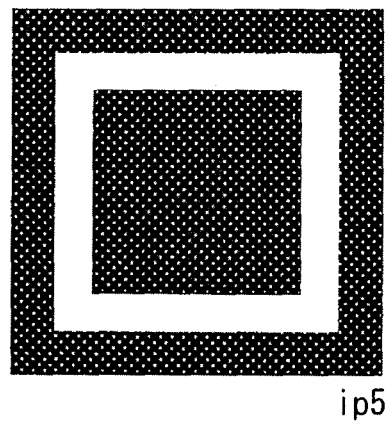

FIG. 5 is a conceptual diagram showing an example of locations, which the monitoring electrodes are placed, in an embodiment of the present invention.

The upper part of FIG. 5 is the front side of the subject to be measured. The location that the monitoring electrode to be placed any one of the left frontal pole part Fp1, the left frontal part F3, the left central part C3, the left parietal part P3, the left occipital part O1, the left middle temporal part T3, the left rear temporal part T5, the frontal part in the middle line Fz, the central part in the middle line Cz, the parietal part in the middle line Pz, the right frontal pole part Fp2, the right frontal part F4, the right central part C4, the right parietal part P4, the right occipital part O2, the right middle temporal part T4 and the right rear temporal part T6 in the cephalic part plane ep1. It also can be placed in any one of the left auriculcar part A1 and the right auriculcar part A2. The reference potential is acquired with the brain activity measurement device 101 by the monitoring electrode placed any one of the left auriculcar part A1 and the right auriculcar part A2. Then, the difference of the electrical potential between the electrical potentials obtained with the different monitoring electrodes and the reference potential is acquired as the element signals of the each brain activity signal.

Explanation of FIG. 3 is resumed below. The presenting information memory device 102 stores the presenting information signal, which represents the presenting information to be presented to the subject to be measures, in association with the presented information identification information. The presenting information signal is an image signal, for example. The presented information identification information is a signal identifying each presenting information signal.

FIG. 6A to FIG. 6D are figures showing examples of the presented information related to an embodiment of the present invention.

FIG. 6A to FIG. 6D indicate the images it1 to it4 as examples of the presented information. Each of the images it1 to it4 is divided into multiple sections horizontally and vertically. They are random dot patterns, the sections of which is in black or white. Usage of these random dot patterns is suitable for distinguishing the status of the brain activity clearly, all over the active area corresponding to the viewing area of the subject to be measured. As a result, this random dot patterns are used in the computation of the individual conversion information, which is described later, and the generation of presented information reconstructing model, for example.

FIG. 7A to FIG. 7E are figures showing other examples of the presented information related to an embodiment of the present invention.

FIG. 7A to FIG. 7E indicate the image ip1 (FIG. 7A), image ip2 (FIG. 7B), image ip3 (FIG. 7C), image ip4 (FIG. 7D) and image ip5 (FIG. 7E) as the presented images. The image ip1 is an image of a black solid square having a smaller white open square in the middle. The image ip2 is an image of black solid square having a smaller white open square in the middle. In addition the smaller white open square includes an even smaller black solid square in the middle. The image ip3 is an image of a black solid square having a white open cross-shape in the middle. The image ip4 is an image of a black solid square having a white open x mark in the middle. The image ip5 is an image of a black solid square having a smaller white open square in the middle. In addition the smaller white open square includes an even smaller black solid square in the middle.

Here, the side length of the smaller white open square in the image ip2 is shorter than that of the image ip5. Also, the width of white part in the image ip2 is narrower than that of the image ip5. Also, the side length of the smallest solid black square in the image ip2 is shorter than that of image ip5.

These images ip1 to ip5 are used in the computation of the presented information categorizing model, which is described later, and measuring the brain activity signals of the source subject used for deducing the brain activity signal of the target subject.

The presented information signals, which the presenting information memory device 102 stores, can be not only the image signal representing an still image, but image signals representing a moving image or audio signals in the present embodiment.

Explanation of FIG. 3 is resumed below again. The information presentation device 103 reads out the presented information signal and a presented information identification code from the presenting information memory device 102. Then, the information presentation device 103 presents the presenting information based on the read out presented information signal to the subject to be measured when the brain activity measurement device 101 acquires the brain activity signals. The information presentation device 103 allows the brain activity signal memory device 104 to store the presented information identification code corresponding to the presented information. The brain activity signal memory device 104 stored the presented information identification code corresponding to the presented information presented by the information presentation device 103 in association with the brain activity signal fed from the brain activity measurement device 101 for each subject in time course.

The noise removal device 114 removes noise elements from the brain activity signal read out from the brain activity signal memory device 104. Then, the noise removal device 114 outputs the brain activity signal that the noise elements have removed to the individual conversion variable computation device 105, the individual conversion device 107, the presented information categorizing model generation device 108, and the presented information reconstructing model generation device 110. The noise removal device 114 includes a high path filter (HPF) whose cutoff frequency is 1/128 Hz, for example. Because of this, the noise removal device 114 removes noise elements having frequencies lower than the cutoff frequency.

The noise removal device 114 may remove noise elements from the brain activity signals fed from the information presentation device 103 and allow the brain activity signal memory device 104 to store the brain activity signals that the noise elements have removed. In that case, the individual conversion variable computation device 105, the individual conversion device 107, the presented information categorizing model generation device 108, and the presented information reconstructing model generation device 110 read out the brain activity signals from the brain activity signal memory device 104 directly.

The individual conversion variable computation device 105 reads out the brain activity signals for each presented information identification code, which were acquired from the two subjects individually, from the brain activity signal memory device 104 via the noise removal device 114. The individual conversion variable computation device 105 evaluates if the brain activity signal memory device 104 has stored brain activity signals corresponding to the identical presented information identification code from at least two subjects or not before reading out the brain activity signals. When operation input signals are input by actions of subjects, the individual conversion variable computation device 105 may readout the brain activity signals of the subject to be measured corresponding to the operation input signals or the presented information identification codes from the brain activity signal memory device 104.

Here, examples of the brain activity signals read out from the individual conversion variable computation device 105 are shown.

Figure 8A:
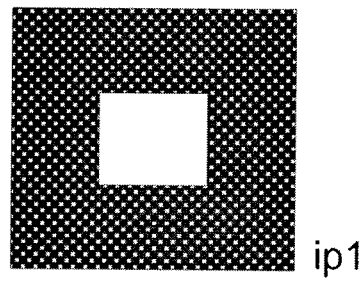
FIG. 8A to FIG. 8C are figures showing other example of the brain activity signal related to an embodiment of the present invention.
Figure 8B:
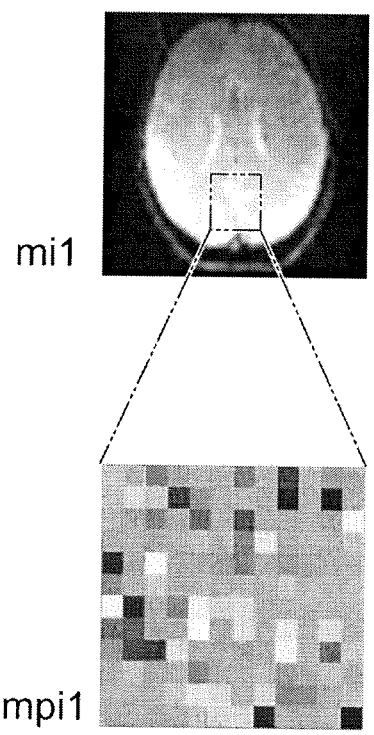
Figure 8C:
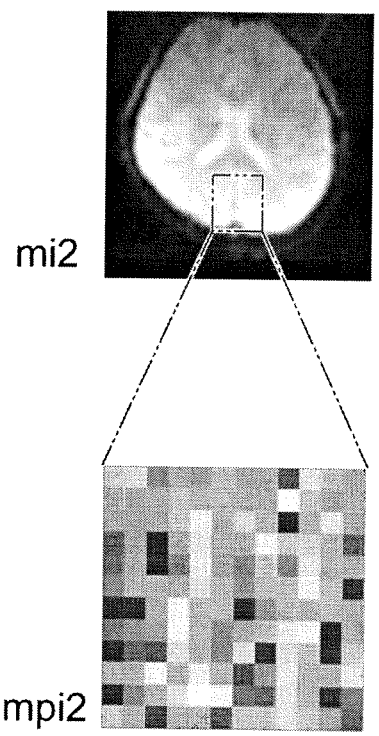

FIG. 8A to FIG. 8C are figures showing other example of the brain activity signal related to an embodiment of the present invention.

FIG. 8A shows the image ip1, which the information presentation device 103 presented to the two subjects to be measured individually. FIG. 8B shows the image mi1, which indicates the brain activity signals obtained from the first subject, and the image mpi1. The rectangular part, which is enclosed with the two-dot chain line at the lower part in the image mi1, and the two-dot chain lines extended from the rectangular shape to the top-left corner and the top-right corner of the image mpi1 indicate that the image mpi1 is the magnified image of the rectangular part of the image mi1.

FIG. 8C shows the image mi1, which indicates the brain activity signals obtained from the second subject, and the image mpi2. The rectangular part, which is enclosed with the two-dot chain line at the lower part in the image mi2, and the two-dot chain lines extended from the rectangular shape to the top-left corner and the top-right corner of the image mpi2 indicate that the image mpi2 is the magnified image of the rectangular part of the image mi1. The rectangular part indicated in the image mi2 is the identical part of the rectangular part indicated in the image mi1.

The grey-scale distribution of the images mpi1 and mpi2 are different. Because of this, it is indicated that the measured brain activity signals are different depending on the subjects to be measured even if the same presentation information is presented in FIGS. 8A to 8C.

The individual conversion variable computation device 105 computes the individual conversion variable (individual conversion information) in order to convert the brain activity signals of the first subject to be measured to that of the second subject to be measured. This computation is performed based on the brain activity signals of the first and second subjects to the same presenting information.

The brain activity signal y of the target subject can be deduced by performing the linear combination (weighting) of the brain activity signal "x_msrd" of the measured source subject based on an individual conversion matrix W as shown in the formula (1) shown below. In the formula (1), the deduced brain activity signal of the target subject is represented by "y_estm." Hereinafter, values are distinguished by suffixes, "_msrd", "_estm", and "_targ", showing the values are a measured value, a deduced value, a targeted value, respectively. In a case where such distinction is not needed, or all the values are included, these suffixes are not used.

$$y\_estm = W x\_msrd \qquad (1)$$

In the formula (1), the brain activity signal y_estm is a vector of $D_y$-dimension ($D_y$ is a natural number of 2 or more, such as 1000) including the element signal value $y_i'\_estm$ of a deduced voxel i. Here, the voxel i means an i-th arbitrary voxel (i is a natural number of 1 or more). The brain activity signal x_msrd of the source subject is a vector of $D_y$-dimension ($D_y$ is a natural number of 2 or more, such as 1000) including the element signal value $x_j$ of the voxel j. Here, the voxel j means a j-th arbitrary voxel (i is a natural number of 1 or more). The individual conversion matrix W is a matrix having $D_y$ rows and $D_x$ columns. The individual conversion matrix W includes a weighting coefficient $w_{ij}$, which the element signal $x_j$ of the voxel j is multiplied to in order to obtain the element signal value $y_i'$. In other words, the individual conversion matrix W shows the correlation between the brain activity signal y_msrd of the target subject and the brain activity signal x_msrd of the source subject. The individual conversion variable computation device 105 computes the individual conversion matrix W in such a way that the deduced brain activity signal y_estm and the brain activity signal y_masd are approximated in the nearest approximation (at the maximum likelihood).

The individual conversion variable computation device 105 performs the sparse regression process in order to compute the individual conversion matrix W, for example. In the sparse regression, the overfitting can be avoided by deleting the feature not contributing to the brain activity signal y of the target subject among the feature based on the brain activity signal x of the source subject. The overfitting means the situation in which the variables, which are the subjects of the training (in this case, the individual conversion matrix W), fit to the training data used for training, but do not fit to unknown data. Effect of noise elements included in the brain activity signal x or the brain activity signal y and the dimension of the individual conversion matrix W can be reduced by avoiding the overfitting. Also, The reduction of the deduction accuracy can be avoided. The sparse regression will be explained later.

The individual conversion variable memory device 106 stores the individual conversion matrix W (individual conversion information) of each pair of the source and target subjects.

The individual conversion device 107 reads out the brain activity signal x_msrd corresponding to the presented information identification code and the source target via the noise removal device 114. Then, the individual conversion device 107 reads out the individual conversion matrix W corresponding to the pair of the source and target subjects from the individual conversion variable memory device 106.

When operation input signals are input by actions of subjects, the individual conversion device 107 may readout the presented information identification code corresponding to the operation input signal and the brain activity signal y_msrd corresponding to the target subject from the brain activity signal memory device 104 via the noise removal device 114. Also, the individual conversion device 107 may readout the individual conversion matrix W corresponding to the pair of the source and target subjects corresponding to the operation input signal from the individual conversion variable memory device 106.

The individual conversion device 107 deduces the brain activity signal y_estm of the target subject based on the individual conversion matrix W reading out the readout brain activity signal x_msrd. Here, the individual conversion device 107 deduces the brain activity signal y_estm of the target subject using the formula (1).

The individual conversion device 107 outputs the deduced brain activity signal y_estm to the conversion information processing device 112.

The presented information categorizing model generation device 108 reads out the brain activity signal y_msrd of a subject to be measured (for example, the target subject) from the brain activity signal memory device 104 via the noise removal device 114. Also, in terms of the presented information code, the presented information categorizing model generation device 108 reads out it from the brain activity signal memory device 104 directly. The presented information categorizing model generation device 108 generates the presented information categorizing model showing an association between the readout brain activity signal y_msrd and the presented information identification information.

Assume that the probability $p_{ip\_estm}$ of the presenting image ip being presented to the target subject can be represented using the normalized exponential function (softmax function) based on the presented information categorizing matrix V of the brain activity signal y as shown in the formula (2) below, when the brain activity signal y of the target subject is given. The normalized exponential function is a function in which is asymptotic to the maximum value of 1 when the variable get closer to the positive infinity, and to the minimum value of 0 when the variable get closer to the negative infinity.

$$p_{ip\_estm} = \frac{\exp\left(\sum_{i=1}^{D_y} v_{ip,i} y_i + v_{ip,0}\right)}{\sum_{ip=1}^{D_{ip}} \exp\left(\sum_{i=1}^{D_y} v_{ip,i} y_i + v_{ip,0}\right)} \quad (2)$$

In the formula (2), $V_{ip,i}$ is an weighting coefficient which the element signal value $y_i$ of the voxel i against the presenting information ip is multiplied to. $v_{ip,0}$ is a bias, which cannot be explained by the brain activity y against the presenting information ip. $D_{ip}$ (a natural number of 2 or more) is the total number of kinds of the presenting information. A matrix including $v_{ip}$, i as an element is called as the presented information categorizing matrix V.

Here, the presented information categorizing model generation device 108 generates element number $D_{ip}$ (number) of the probability vector p_estm including the probability $p_{ip\_estm}$ as an element.

The presented information categorizing model generation device 108 generates the target probability vector p_targ representing the presenting information ip based on the readout presented information identification code (that is, the code ip).

The target probability vector p_targ is a vector including $D_{ip}$ (number) of the element value $p_{ip}$. Here, the presented information categorizing model generation device 108 sets the ip'-th element value $p_{ip\_}$targ and the other element values (ip≠ip') to 1 and 0, respectively, when the presenting information ip' is presented. In the other words, the presented information categorizing matrix V is a matrix having $D_{ip}$ rows and $D_y+1$ columns, and shows the correlation between the brain activity signal y_msrd of the target subject and the target probability vector p_targ representing the related presenting information. The numbers in the raw includes the bias $v_{ip,0}$ for each presenting information.

The presented information categorizing model generation device 108 computes the presented information categorizing matrix V in such a way that the deduced probability vector p_estm and the target probability vector p_targ are approximated in the nearest approximation (for example, at the maximum likelihood).

The presented information categorizing model generation device 108 computes the presented information categorizing matrix V based on the brain activity signal y, the target probability vector p_targ, and the deduced probability vector p_estm by performing the sparse regression which will be explained later, for example. By the sparse regression, the dimension of the presented information categorizing matrix V is reduced and reduction of the deduction accuracy is prevented. The presented information categorizing model generation device 108 performs the sparse regression using the probability vector p_estm and the presented information categorizing matrix V computed by using the formula (2) with the brain activity signal y_msrd and the target probability vector p_targ, instead of the deduced brain activity signal y_estm and the individual conversion matrix W computed by using the formula (1) with the brain activity signal x_msrd and the brain activity signal y_msrd, respectively.

The presented information categorizing model generation device 108 computes the average value $<v_{ip,i}>$ of the categorizing weighting coefficients for each element in the sparse regression which will be explained later. The presented information categorizing model generation device 108 allows the presented information categorizing model memory device 109 to store the presented information categorizing matrix V, which includes the computed average value $<v_{ip,i}>$ of the categorizing weighting coefficients as an element value (categorizing weighting coefficient $v_{ip,i}$).

The presented information categorizing model memory device 109 stores the presented information categorizing matrix V as an presented information categorizing model for each presenting information.

The presented information reconstructing model generation device 110 reads out the brain activity signal y_msrd of the subject to be measured (for example, the target subject) and the presented information identification code from the brain activity signal memory device 104 via the noise removal device 114. Then, the presented information reconstructing model generation device 110 reads out the presenting information ip corresponding to the readout presented information identification code from the presenting information memory device 102.

The presented information reconstructing model generation device 110 reads out the presented feature information from the presented information reconstructing model memory device 111. This presented feature information is a local basis image (local image basis) $\phi_m$, for example. The letter "m" is a local basis image identification code for identifying each local basis image.

The local basis image is a image signal showing a part of region in a single frame (1-frame) image (whole image). The local basis image includes one or more of images, and maybe one selected from an image of 1 pixel horizontally and 1 pixel vertically, an image of 1 pixel horizontally and 2 pixels vertically, image of 2 pixels horizontally and 1 pixel vertically, and an image of 2 pixels horizontally and 2 pixels vertically, for example. The signal value of each pixel has a value indicating that the pixel is included in the local basis image (for example, 1) or a value indicating that the pixel is not included in the local basis image (for example, 0).

The presented information reconstructing model generation device 110 generates the presented information reconstructing model for reconstructing the image signal as the presenting information based on the readout brain activity signal y_msrd and the local basis image as the presented feature information.

For example, when the brain activity signal y of the target subject is given, the image signal F_estm (r|y) representing the 1-frame image, which is the presenting information ip, can be expressed by a linear combination, which is a product of the local basis image $\phi_m$ (r) and the deduced contrast $C_{m\_estm}$ (y) as shown in the formula (3) below, for example.

$$F_{\_estm}(r \mid y) = \sum_{m=1}^{M} \lambda_m C_{m\_estm}(y) \phi_m(r) \quad (3)$$

In the formula (3), "r" represent the pixel location included in the image signal. "m" is the identification code identifying each local basis image. "M" is the number of the local basis images. "$\lambda_m$" is the combination coefficient that the contrast $C_{m\_estm}$ (y) is multiplied to. The contrast $C_{m\_estm}$ (y) is the value indicating the contrast density of each local basis image. The local basis image $\phi_m$ (r) has the signal value of 1 when the location r is included in the region of the local basis image. It has the signal value of 0 when the location r is not included in the region.

Here, it is assumed that the contrast $C_{m\_estm}$ (y) can be expressed by a liner combination of the brain activity signal y of the target subject as shown in the formula (4) below, for example.

$$C_{m\_estm}(y) = \sum_{i=1}^{D_y} u_{mi} y_i + u_{m0} \qquad (4)$$

In the formula (4), "$u_{mi}$" is the contrast weighting coefficient that the element signal value y of the voxel i is multiplied to. Here, the vector that includes the contrast $C_m\_estm$ as an element is called as the contrast vector VC_estm. The contrast vector VC_estm is a vector having $D_y+1$ columns. The matrix containing the contrast weighting coefficient $u_{mi}$ as an element is called as the contrast matrix U. The contrast matrix U is a matrix having M rows and $D_y+1$ columns. The numbers in a column includes the bias value $u_{mo}$ for each local basis image $\phi_m$. In other words, the contrast matrix U indicates the correlation between the brain activity y of the target subject and the contrast $C_m\_estm$ for each local basis image.

Here, the presented information reconstructing model generation device 110 deduces the contrast vector VC_estm with M (number) of elements. The presented information reconstructing model generation device 110 includes the contrast $C_m\_estm$ (y_msrd) as an element.

The presented information reconstructing model generation device 110 extracts the image signal F_targ (r) in the region r occupied by the local basis image $\phi_m$ from the presenting information ip presented to the target subject as the contrast $C_m\_targ$, which is the target for each local basis image m. The presented information reconstructing model generation device 110 generates the target contrast vector VC_targ including the extracted contrast $C_m\_targ$.

The presented information reconstructing model generation device 110 computes the contrast matrix U in such a way that the deduced contrast vector VC_estm and the target contrast vector VC_targ are approximated in the nearest approximation (for example, at the maximum likelihood).

The presented information reconstructing model generation device 110 computes the contrast matrix U based on the brain activity y, the target contrast vector VC_targ, and the deduced contrast vector VC_estm, for example by performing the sparse regression which is explained later. By the sparse regression, the dimension of the contrast matrix U can be reduced, and reduction of deduction accuracy can be avoided. The presented information reconstructing model generation device 110 performs the sparse regression using the contrast vector VC_estm and the contrast matrix U computed by using the formula (4) with the brain activity signal y and the target contrast signal VC_targ, instead of the deduced brain activity signal y_estm and the individual conversion matrix W computed by using the formula (1) with the brain activity signal x_msrd and the brain activity signal y_msrd, respectively.

presented information reconstructing model generation device 110 computes the average value $<u_{mi}>$ of the contrast weighting coefficients for each element in the sparse regression, which is explained later. The presented information reconstructing model generation device 110 allows the presented information reconstructing model memory device 111 to store the contrast matrix U containing the computed average value $<u_{mi}>$ of the contrast weighting coefficients as an element value $u_{mi}$.

The presented information reconstructing model generation device 110 generates the contrast vector VC_estm for each presenting information ip using the formula (4).

The presented information reconstructing model generation device 110 deduces the image signal F_estm (r|y) based on the contrast vector VC_estm generated for each presenting information ip, the combination coefficient $\lambda_m$, and the local basis image $\phi_m$ (r) using the formula (3).

Here, the presented information reconstructing model generation device 110 computes the combination coefficient $\lambda_m$ in such a way that the error between the deduced image signal F_estm (r|y) and the original image information F_targ (r|y) is minimum, for example using the mean square method.

The presented information reconstructing model generation device 110 allows the presented information reconstructing model memory device 111 to store the computed combination coefficient $\lambda_m$.

The presented information reconstructing model memory device 111 stores the local basis image $\phi_m$ (r), the combination coefficient $\lambda_m$, and the contrast matrix U as the presented information reconstructing model.

The conversion information processing device 112 processes the target subject's brain activity signal y_estm fed from the individual conversion device 107. Then, the conversion information processing device 112 deduces the information that are processed in the brain of the target subject, the information being the presenting information presented to the target subject.

The conversion information processing device 112 includes the presented information categorizing device 1121 and the presented information reconstruction device 1122, for example.

The brain activity signal y_estm is input to the presented information categorizing device 1121 from the individual conversion device 107. Then, the presented information categorizing device 1121 reads out the presented information categorizing matrix V for each presenting information from the presented information categorizing model memory device 109.

The presented information categorizing device 1121 computes the probability $p\_estm_{ip}$ based on the brain activity signal y_estm and the presented information categorizing matrix V for example using the formula (2). The presented information categorizing device 1121 determines the presented information with the highest of the computed probability $p\_estm_{ip}$.

As explained above, the presented information categorizing device 1121 assumes (discriminates) the presenting information presented to the target subject during acquisition of the brain activity signal y to be the determined presenting information ip.

The brain activity signal y_estm is input to the presented information reconstruction device 1122 from the individual conversion device 107. Then, the presented information reconstruction device 1122 reads out the local basis image $\phi_m$ (r), the combination coefficient $\lambda_m$ for each presenting information, and the contrast matrix U, from the presented information reconstructing model memory device 111.

The presented information reconstruction device 1122 computes the contrast vector VC_estm based on the brain activity signal y_estm and the readout contrast matrix U, for example using the formula (2).

The presented information reconstruction device 1122 performs the reconstruction of the presenting information by computing the image signal F_estm (r|y_estm) based on the computed contrast vector VC_estm, the readout local basis image $\phi_m$ (r), and the combination coefficient $\lambda_m$ for each presenting information, for example using the formula (3).

As explained above, the conversion information processing device 112 assumes the presenting information presented to the target subject during acquisition of the brain activity signal y to be the image showing the reconstructed image signal F_estm (r|y_estm).

Next, the presenting information reconstructed by the presented information reconstruction device 1122 related to the present embodiment is explained.

FIG. 9 is a figure showing examples of presented information reconstructed by the reconstructed model generation device related to an embodiment of the present invention.

FIG. 9 is a figure showing examples the presenting image that the presented information reconstruction device 1122 related to the present embodiment have reconstructed.

FIG. 9 shows the images ip1 to ip5 from top to bottom on the left column as the presenting information. On the middle column, the images ip1' to ip5', which were reconstructed based on the brain activity signals measured from the target subject during presentation of each images ip1 to ip5, are shown. In the other words, the images ip1' to ip5' are the images that the presented information reconstruction device 1122 has reconstructed based on the brain activity signal obtained from the target subject and the presented information reconstructing model of the target subject himself (target subject reconstructed image). On the right column of FIG. 9, the images ip1" to ip5", which are the images deduced based on the brain activity signal of the source subject during presenting each images ip1 to ip5, are shown. In other words, the images ip1" to imp5" are the images that the presented information reconstruction device 1122 has deduced based on the brain activity signal obtained from the source subject, who is different from the target subject, and the presented information reconstructing model of the target subject himself (source subject reconstructed image).

FIG. 9 shows that target subject reconstructed image and the source subject reconstructed image retain the feature of the presenting information. For example, the central part is white and the peripheral part is filled dark in the images ip1' and ip1". Such a feature is shared with the image ip1. In the images ip2' and ip2", the central part contains a white-lined rectangle and the peripheral part is filled dark. Such a feature is shared with the image ip2. In the images ip3' and ip3", the central part contains the white parts extending horizontally and vertically. Such a feature is shared with the image ip3. In the images ip4' and ip4", there are white parts extending diagonally. Such a feature is shared with the image ip4. In the images ip5' and ip5", there is a part filled dark in the middle, and there is white part around the part filled dark. Such a feature is shared with the image ip5.

Next, an example of the brain activity measurement process performed by the brain activity deducing apparatus related to the present embodiment is explained.

FIG. 10 is a flowchart showing an example of the brain activity measuring process performed by the brain activity deducing apparatus related to an embodiment of the present invention.

[Step S101]

In the step S101 the measured signal generation device 1011 generates the measurement signal representing the magnetic field signal, which is transmitted. This generated signal is output to the measured signal transmission device 1012. Then, the process proceeds to the step S102.

[Step S102]

In the step S102, the measured signal transmission device 1012 generates a magnetic field based on the measured signal fed from the measured signal generation device 1011. Then, this generated magnetic field is presented to the cephalic part of the subject to be measured. Then, the process proceeds to the step S103.

[Step S103]

In the step S103, the information presentation device 103 present the presenting information based on the presented information signal readout from the presenting information memory device 102 to the subject to be measured. The presenting information is for example one of the images it1 to it4 shown in FIGS. 6A to 6D, or a random dot pattern similar to the images. The presented information identification code corresponding to the presenting information presented by the information presentation device 103 is stored by the brain activity signal memory device 104. Then, the process proceeds to the step S104.

[Step S104]

In the step S104, the brain activity signal reception device 1013 receives the brain activity signal representing the activity for each voxel of the cephalic part of the subject to be measured. The brain activity that the brain activity signal reception device 1013 receives is output to the noise removal device 1014. Then, the process proceeds to the step of S105.

[Step S105]

In the step S105, the noise removal device 1014 removes the noise element from the brain activity signal fed from the brain activity signal reception device 1013. The brain activity signal, the noise element of which is removed, is stored by the brain activity signal memory device 104. Then, the process proceeds to the Step S106.

[Step S106]

In the step S106, the individual conversion variable computation device 105 determine if the brain activity signal memory device 104 hold the brain activity signal of at least two subject to be measured or not, the brain activity signal corresponding to the same presenting image.

In a case where the individual conversion variable computation device 105 determines that the brain activity signal memory device 104 does not hold the brain activity signal of 2 or more of the subjects (the option NO in the step S106), the process proceeds to the step S101. In a case where the individual conversion variable computation device 105 determines that the brain activity signal memory device 104 holds the brain activity signal of 2 or more of the subjects (the option YES in the step S106), the process proceeds to the step S107.

[Step S107]

In the step S107, the individual conversion variable computation device 105 reads out the brain activity signals individually acquired from two subjects to be measured from the brain activity signal memory device 104. One of the subjects is the source subject, and another is the target subject. The individual conversion variable computation device 105 computes the individual conversion matrix W including the individual conversion variable (weighting coefficient) as an element in such a way that the brain activity signal of the target subject deduced based on the brain activity signal of the source target and the measured brain activity signal of the targeted subject are approximated in the nearest approximation (at the maximum likelihood). The individual conversion variable computation device 105 performs the sparse regression treatment which is explained later in order to compute the individual conversion matrix W. Then, the process proceeds to the step S108.

[Step S108]

In the step S108, the individual conversion variable memory device 106 stores the individual conversion matrix W, which is computed by the individual conversion variable computation device 105 and includes the average value $<w_{ij}>$ of the weighting coefficients as an element (weighting coefficient $w_{ij}$). Then, the process is finished.

Next, an example of a brain activity deducing process performed by the brain activity deducing apparatus 1 related to the present embodiment is explained.

Figure 11:
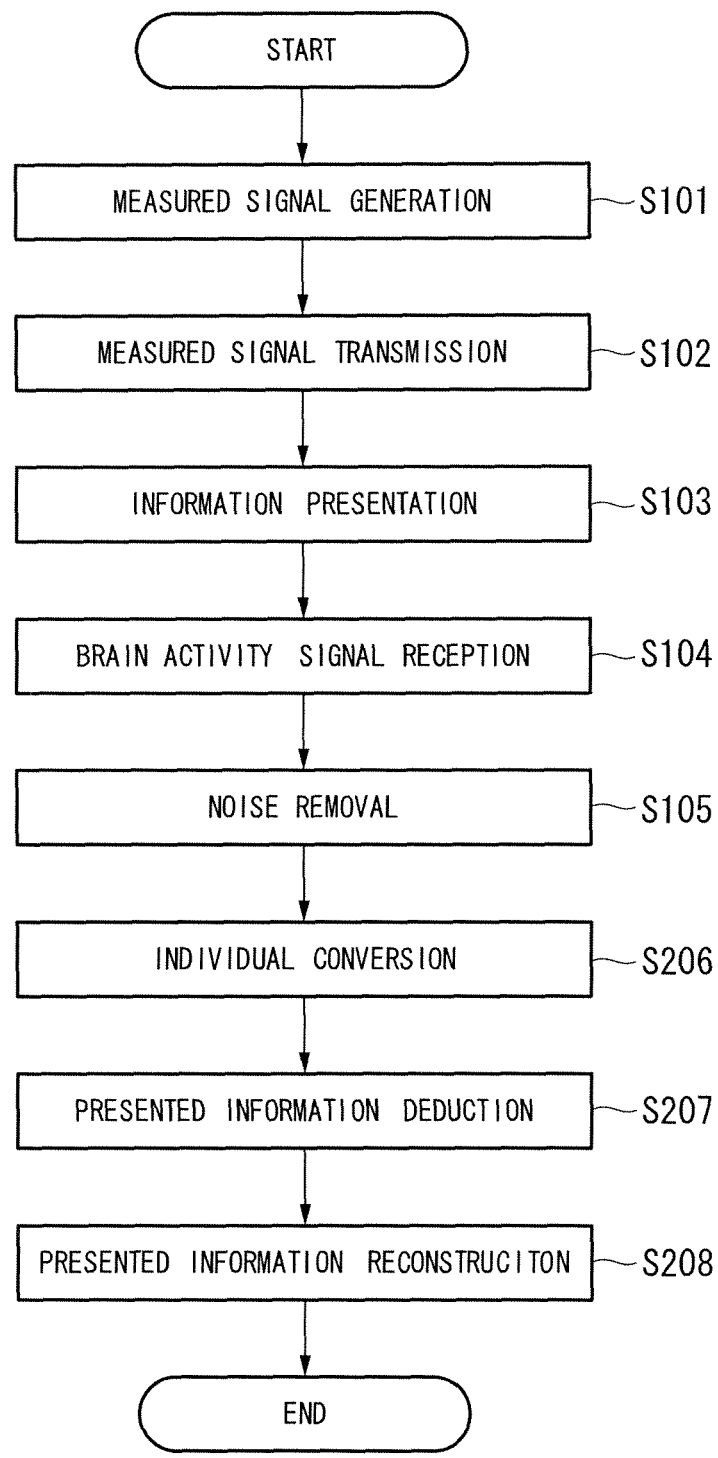
FIG. 11 is a flowchart showing an example of the brain activity deducing process performed by the brain activity deducing apparatus related to an embodiment of the present invention.

FIG. 11 is a flowchart showing an example of the brain activity deducing process performed by the brain activity deducing apparatus related to an embodiment of the present invention.

This example is the same to the brain deducing process shown in FIG. 10, in the point that the steps S101 to S105, which are the steps for obtaining the brain activity signal, are performed at the beginning of the process. On the other hand, it is different in the point that the process proceeds to the step S206 after the step S105 in this example. Also, the information presentation device 103 presents the images ip1 to ip5 shown in FIGS. 7A to 7E, or the images similar to them to the subject to be measured as the presenting information in the S103 in this example.

Step S206 and steps after the step S206 are explained below.

[Step S206]

In the step S206, the individual conversion device 107 reads out the presented information identification code and the brain activity signal y_msrd of the source subject from the brain activity signal memory device 104. And then, the individual conversion device 107 reads out the individual conversion matrix W corresponding to the pair of the source and target subjects from the individual conversion variable memory device 106.

The individual conversion device 107 deduces the brain activity signal x_msrd based on the individual conversion matrix W. Also individual conversion device 107 deduces the brain activity y_estm, for example using the formula (1).

The brain activity signal y_estm deduced by the individual conversion device 107 is output to the presented information categorizing device 1121 and the presented information reconstruction device 1122 of the conversion information processing device 112. Then, the process proceeds to the step S207.

[Step S207]

In the step S207, the brain activity signal y_estm of the target subject is input to the presented information categorizing device 1121 from the individual conversion device 107. Also, the presented information categorizing device 1121 reads out the presented information categorizing matrix V for each presenting information from the presented information categorizing model memory device 109.

The presented information categorizing device 1121 computes the probability $p_{ip\_}$estm based on the brain activity signal y_estm and the presented information categorizing matrix V, for example using the formula (2). The presented information categorizing device 1121 assumes (discriminates) the presenting information ip having the highest computed probability $p_{ip\_}$estm. Then, the process proceeds to the step S208.

[Step S208]

In the step S208, the brain activity signal y_estm of the target subject is input to the presented information reconstruction device 1122 from the individual conversion device 107. Also, the presented information reconstruction device 1122 reads out the local basis image $\phi_m(r)$, the combination coefficient $\lambda_{m,ip}$ for each presenting information, and the contrast matrix U from the presented information reconstructing model memory device 111.

The presented information reconstruction device 1122 computes the contrast $C_{m\_}$estm based on the brain activity signal y_estm and the contrast matrix U, for example using the formula (4). Then, the presented information reconstruction device 1122 generates the contrast vector VC_estm including the computed contrast $C_{m\_}$estm as an element. The presented information categorizing device 1121 reconstructs the image signal F_estm (r|y_estm) based on the computed contrast vector VC_estm, the readout local basis image $\phi_m(r)$, and combination coefficient $\lambda_{m,ip}$, for example using the formula (3). Then, the process is finished.

In the brain activity deducing process shown in FIG. 11, the timing that the step S208 is performed can be before the timing that the step S207 is performed. Alternatively, the steps S207 and S208 can be performed concurrently.

Also, only one of the steps S207 and S208 maybe performed in this process.

Next, the sparse regression related to the present embodiment is explained. It is presupposed that the individual conversion variable computation device 105 computes the average value $<w_{ij}>$ of the weighting coefficients based on the brain activity signal x_msrd, the brain activity signal y_msrd, the deduced brain activity signal y_estm, and the individual conversion matrix W.

Also, the presented information categorizing model generation device 108 computes the average value $<v_{ip,i}>$ of the category weighting coefficients based on the each brain activity signal y_msrd, the target probability vector p_targ, and the probability vector p_estm, instead of the brain activity signal x_msrd, the brain activity signal y_msrd, the deduced brain activity signal y_estm, and the individual conversion matrix W.

Also, the presented information reconstructing model generation device 110 computes the average value $<u_{mi}>$ of the contrast weighting coefficients based on the brain activity signal y_msrd, the target contrast signal VC_targ, and the deduced contrast vector VS_estm, instead of the brain activity signal x_msrd, the brain activity signal y_msrd, the deduced brain activity signal y_estm, and the individual conversion matrix W.

Figure 12:
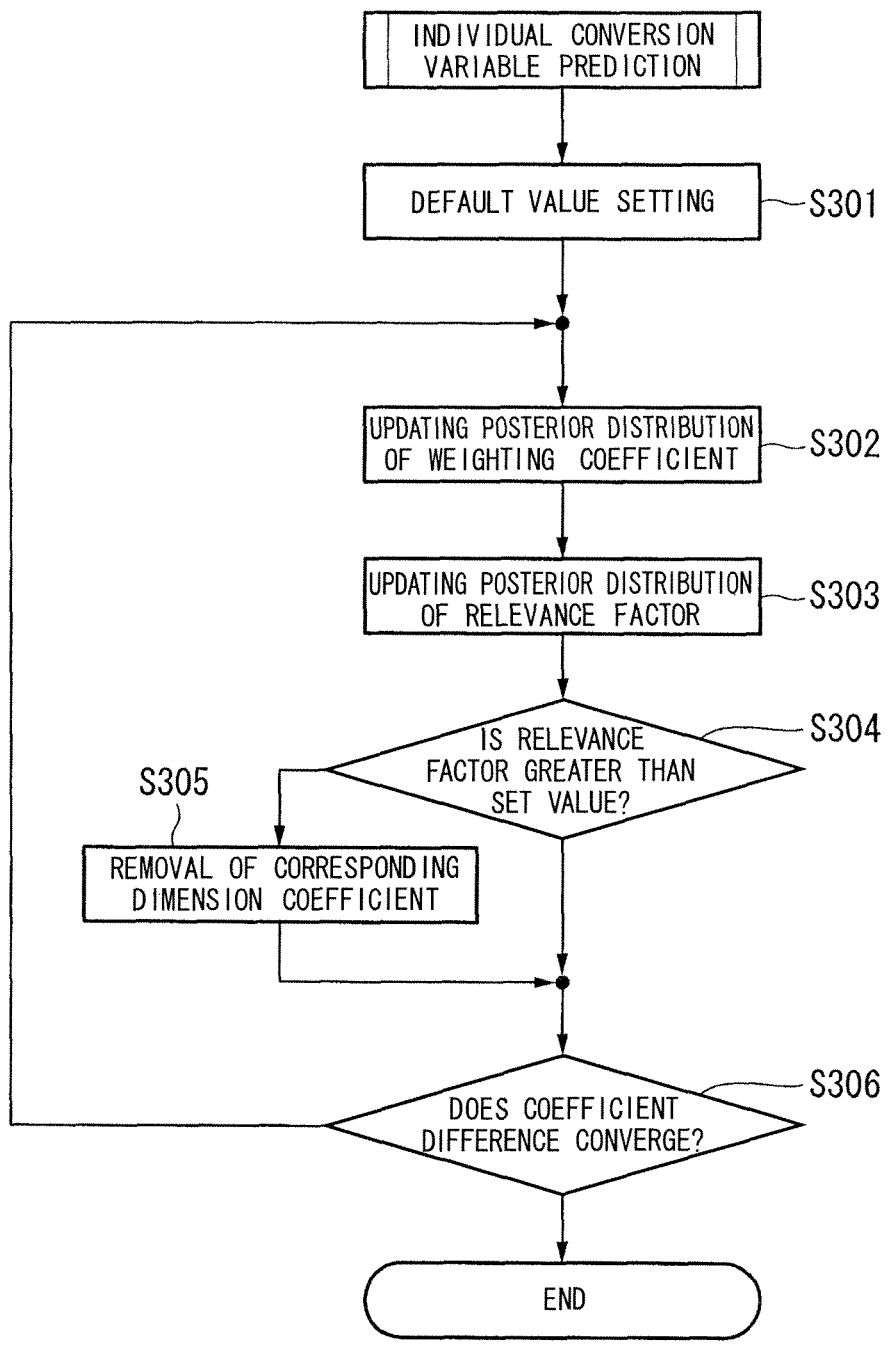
FIG. 12 is a flowchart showing an example of the sparse regression process related to an embodiment of the present invention.

FIG. 12 is a flowchart showing an example of the sparse regression process related to an embodiment of the present invention.

[Step S301]

In the step S301, the individual conversion variable computation device 105 sets the default values of the dimension $D_x$ of the brain activity signal x, the dimension of $D_y$ of the brain activity signal y, and the anticipated value $<\alpha_{ij}>$ of the relevance parameter $\alpha_{ij}$ as variables needed for the process. The relevance parameter $\alpha_{ij}$ is an real number showing the degree of relevance of the voxel i, the brain activity signal y of which includes the element signal of the voxel i included in the brain activity x, to the element signal, and larger than 0. The relevance parameter $\alpha_{ij}$ is the coefficient for assuming the ARD prior (Automatic Relevance Determination prior) in the sparse regression.

In the ARD prior, the average (mean) of the conditional probability $P(w_{ij}|\alpha_{ij})$ of the weighting coefficient $w_{ij}$ against the relevance parameter $\alpha_{ij}$ is assumed to be 0. Also, it is assumed that it is distributed according to a normal distribution (Gaussian distribution) with the variance of $\alpha_{ij}^{-1}$, N (0, $\alpha_{ij}^{-1}$). In other words, the higher the relevance parameter $\alpha_{ij}$, the lower the relevance of the voxel i included in the brain activity signal y to the element signal.

In the ARD prior, the probability $P_0(\alpha_{ij})$ that has the relevance parameter of $\alpha_{ij}$ is assumed to be $\alpha_{ij}^{-1}$.

After that, the process proceeds to the step S302.

[Step S302]

In the step S302, the individual conversion variable computation device 105 performs the hierarchical Baysian estimation with the provided brain activity signal x_msrd and posterior distribution Q(A) of the brain activity signal y_msrd and the relevance parameter $\alpha_{ij}$. Then, the individual conversion variable computation device 105 updates the posterior distribution Q(W) of the weighting coefficient $w_{ij}$. In the hierarchical Baysian estimation, the individual conversion variable computation device 105 computes the average value $<w_{ij}>$ of the weighting coefficient $w_{ij}$, which defines the posterior distribution Q(W), and the covariance $S_{ij}$ in such a way that the variational free energy becomes the highest value.

Here, the individual conversion variable computation device 105 computes the average value $<w_{ij}>$ of the weighting coefficient $w_{ij}$ in such a way that the free energy E(W), which is represented by the formula (5) below, becomes the highest value, based on an assumption that the weighting coefficient $w_{ij}$ is assumed to distribute according to the multidimensional Gaussian distribution.

$$E(W) = \sum_{n=1}^{N}\left[\sum_{i=1}^{D_y}\sum_{j=1}^{D_x} y^{(n)}_{i\_msrd} w_{ij} x^{(n)}_{j\_msrd} - \log\left(\sum_{i=1}^{D_y}\sum_{j=1}^{D_x} \exp(w_{ij} x^{(n)}_{j\_msrd})\right)\right] - \quad (5)$$

$$\frac{1}{2}\sum_{i=1}^{D_y}\sum_{j=1}^{D_x} w_{ij} \langle \alpha_{jj} \rangle w_{ji}$$

In the formula (5), n is the number for identifying the pair of the brain activity signal x and the brain activity signal y obtained by presenting the same information to the source and target subjects. Also, N is the number of the pair of the brain activity signal x and the brain activity signal y. Also, $<\alpha_{ij}>$ is the on-diagonal element of the anticipated value in a case where the relevance factor $\alpha_{ij}$ is assumed to distribute according to the Gamma distribution.

Here, the first term in the left-hand member indicates contribution by correlation between the measured brain activity signal y_msrd and estimated brain activity signal y_estm. Also, the second term in the left-hand member indicates contribution of entropy due to the distribution of the estimated brain activity signal y_estm. Also, the third term in the left-hand member indicates contribution of entropy due to the distribution of the relevance factor $\alpha_{ij}$.

In order to maximize the free energy E(W), the individual conversion variable computation device 105 use the Newton method based on the gradient vector represented by the formula (6) below and the Hessian Matrix represented by the formula (7) below, for example.

$$e'_i = \frac{\partial E}{\partial w_{ij}} = \sum_{n=1}^{N}(y^{(n)}_{i\_msrd} - y^{(n)}_{i\_estm})x_{j\_msrd} - \langle \alpha_{ii} \rangle w_{ij} \quad (6)$$

$$(i = 1, \ldots, D_y)$$

In the formula (6), $e'_i$ is an element of the gradient vector $E' = [e'_1, \ldots, e'_{D_y}]$.

$$e''_{ij} = \frac{\partial^2 E}{\partial w_{ij} \partial w_{ij}^T} \quad (7)$$

$$= -\sum_{n=1}^{N}\left(\begin{bmatrix} y^{(n)}_{1\_estm} & 0 & \cdots & 0 \\ 0 & y^{(n)}_{2\_estm} & & \vdots \\ \vdots & & \ddots & 0 \\ 0 & \cdots & 0 & y^{(n)}_{D_y\_estm} \end{bmatrix} - \begin{bmatrix} y^{(n)}_{1\_estm}y^{(n)}_{1\_estm} & y^{(n)}_{1\_estm}y^{(n)}_{2\_estm} & & \\ y^{(n)}_{2\_estm}y^{(n)}_{1\_estm} & y^{(n)}_{2\_estm}y^{(n)}_{2\_estm} & & \vdots \\ & & \ddots & \\ & \cdots & & y^{(n)}_{D_y\_estm}y^{(n)}_{D_y\_estm} \end{bmatrix}\right) \otimes$$

$$x^{(n)}_{j\_msrd} x^{(n)T}_{j\_msrd}$$

In the formula (7), $e''_{ji}$ is an element of the gradient vector $E'' = [e''_{11}, \ldots, e''_{D_yD_y}]$. Also, T indicates the transposition of the vector or the matrix. The circle symbol with a christcross inside indicates it is the Kronecker product.

The individual conversion variable computation device 105 repeats a process for maximizing the above-described function E(W) until the computed average value $<w_{ij}>$ converges. The individual conversion variable computation device 105 counts that the average value $<w_{ij}>$ converges and the function E(W) is maximized when the absolute value of the difference to the previously computed average value $<w_{ij}>$ becomes smaller than a predetermined value.

Next, the individual conversion variable computation device 105 computes the inverse matrix $E''^{-1}$ of the Hessian matrix E'' of the function E(W), in which the weighting coefficient $w_{ij}$ is maximized, as the covariance matrix S. The covariance matrix S is a matrix containing the covariance $S_{ij}^{ij}$ as an matrix element. Then, the process proceeds to the step S303.

[Step S303]

In the step S303, the individual conversion variable computation device 105 updates the posterior distribution Q(A) of the relevance factor $\alpha_{ij}$ with the given brain activity signal x_msrd, the brain activity signal y_msrd, and the posterior distribution Q(W) of the weighting coefficient $w_{ij}$. The individual conversion variable computation device 105 updates the average value $<\alpha_{ij}>$ of the relevance factor $\alpha_{ij}$, which defines the posterior distribution Q(A) based on an assumption that the relevance factor $\alpha_{ij}$ distributes according to the Gamma distribution $\Gamma(\frac{1}{2}, <\alpha_{ij}>)$ with a degree of freedom of ½.

The individual conversion variable computation device 105 updates the average value $<\alpha_{ij}>$ using the formula (8) below.

$$\langle \alpha_{ij} \rangle = \frac{1}{\langle w_{ij} \rangle^2 + S_{ii}^{ij}} \quad (8)$$

The individual conversion variable computation device 105 may update the average value $<\alpha_{ij}>$ using the formula (9) below instead of the formula (8).

$$\langle \alpha_{ij} \rangle = \frac{1 - \langle \alpha_{ij} \rangle S_{ii}^{ij}}{\langle w_{ij} \rangle^2} \quad (9)$$

Then, the step proceeds to the step S304.

[Step S304]

In the step S304, the individual conversion variable computation device 105 evaluates if the average value $\langle\alpha_{ij}\rangle$ of the relevance factor is greater than threshold values that have been pre-set individually, and existence or non-existence of the relevance factor greater than the threshold values is determined. If it is determined that there is an average value $\langle\alpha_{ij}\rangle$ of the relevance factor that is greater than the pre-set threshold value (for example, $10^8$) by the individual conversion variable computation device 105 (option "YES" in the step S304), the process proceeds to the step S305. If it is determined that there is not an average value $\langle\alpha_{ij}\rangle$ of the relevance factor that is greater than the pre-set threshold value by the individual conversion variable computation device 105 (option "NO" in the step S304), the process proceeds to the step S306.

[Step S305]

In the step S305, the individual conversion variable computation device 105 excludes the weighting coefficient $w_{ij}$ of a dimension corresponding to the average value $\langle\alpha_{ij}\rangle$ of the relevance factor greater than the pre-set threshold value in the downstream processes. Specifically, the individual conversion variable computation device 105 sets the weighting coefficient $w_{ij}$ and the average value $\langle\alpha_{ij}\rangle$ at the dimension to 0 on a constant basis. Because of this, the weighting coefficient, which has a low relevance between the element signal of the voxel i included in the brain activity signal y_msrd to the element signal of the voxel j included in the brain activity signal x_msrd, is excluded. Then, the process proceeds to the step S306.

[Step S306]

In the step S306, the individual conversion variable computation device 105 evaluates if the average value $\langle\alpha_{ij}\rangle$ of the relevance factor, the average value $\langle w_{ij}\rangle$ of the weighting coefficient, or the covariance $S_{ij}$ has converged or not. The evaluation if the above-described values have converged or not by the individual conversion variable computation device 105 is done based on the fact that the absolute value of the difference to the previous value is less than a pre-set threshold or not, on these coefficients as a whole or a part of.

In a case where the individual conversion variable computation device 105 determined that the average value $\langle\alpha_{ij}\rangle$ of the relevance factor, the average value $\langle w_{ij}\rangle$ of the weighting coefficient, or the covariance $S_{ij}$ has converged (option "YES" in the step S306), the computed average value $\langle w_{ij}\rangle$ of the weighting coefficient is allowed to be stored by the individual conversion variable memory device 106 as the individual conversion matrix W of the source subject and the target subject. Then, the process is finished. In the other words, the stored individual conversion matrix W includes the computed average value $\langle w_{ij}\rangle$ of the weighting coefficient as an element (weighting coefficient $w_{ij}$).

In a case where the individual conversion variable computation device 105 determines that the average value $\langle\alpha_{ij}\rangle$ of the relevance factor, the average value $\langle w_{ij}\rangle$ of the weighting coefficient, or the covariance $S_{ij}$ has not converged (option "NO" in the step S306), the process proceeds to the step S302.

The individual conversion variable computation device 105 may determine weather the repetition number has reached to a pre-set repetition number or not, instead of determining if the average value $\langle\alpha_{ij}\rangle$ of the relevance factor, the average value $\langle w_{ij}\rangle$ of the weighting coefficient, or the covariance $S_{ij}$ has converged or not in the step S306. In this case, if the individual conversion variable computation device 105 determines that it has reached to the pre-set repetition number, the process is finished. If the individual conversion variable computation device 105 determines that it has not reached to the pre-set repetition number, the process proceeds to the step S302.

In a case where the individual conversion variable computation device 105 and the individual conversion device 107 compute the element signal value $y_{i\_estm}$ of the brain activity signal counting on the bias value $w_{i0}$ of the weighting coefficient as indicated in the formula (10) below, the individual conversion variable computation device 105 and the individual conversion device 107 set and compute relevance factor $\alpha_{i0}$ corresponding to the bias value $w_{i0}$, their average values $\langle w_{i0}\rangle$ and $\langle\alpha_{i0}\rangle$, respectively, in the above-described sparse estimation treatment.

$$y_{i\_estm} = \sum_{j=1}^{D_X} w_{ij} x_{j\_estm} + w_{i0} \qquad (10)$$

In this case, the index j of the bias value $w_{ij}$ and the relevance factor $\alpha_{ij}$ is not 1 but 0 in the formulae (5), (6), and (7).

In the explanation above, the individual conversion variable is computed using a linear Sparse regression, the brain activity signal is linearly-transformed using the computed individual conversion variable. However, non-linear transformation may be performed instead of the linear transformation in the present embodiment. For example, the kernel method can be used in the non-linear transformation in the present embodiment.

Conventionally, an identical model is used to the source targets in the transformation attempt of the brain activity signal. However, different individual conversion variables are used as a model depending on the source targets in the present embodiment. Therefore, a transformation mode can be chosen from the non-linear and linear transformations depending on the source targets.

Also in the explanation above, an example, in which the presented information categorizing model generation device 108 generates the presented information categorizing model based on the brain activity signal y_msrd (measured value) of the target subject and the presented information identification code, was explained. Also, an example, in which the presented information categorizing device 1121 discriminates the presenting information using the probability for each presenting information computed based on the brain activity signal y_estm (estimated value) and the presented information categorizing model, was explained.

However, the presented information categorizing model generation device 108 may generates the presented information categorizing model based on the brain activity signal y_estm (estimated value), which the individual conversion device 107 generates based on the y_msrd (measured value) and the presented information identification code, instead of the y_msrd (measured value) of the target subject in the present embodiment. In this case, the presented information categorizing device 1121 may discriminate the presenting information using the probability for each presenting information computed based on the brain activity signal y_estm (estimated value) and the generated presented information identification model.

Also in the explanation above, an example, in which the presented information reconstructing model generation device 110 generates the presented information reconstructing model based on the brain activity signal y_msrd (measured value) of the target subject, the presented information identification code, and the local basal image, was explained.

Also, an example, in which, was explained. Also, an example, in which the presented information reconstruction device 1122 reconstructs the presented information based on the brain activity signal y_estm (estimated value) and the generated presented information reconstructing model, was explained.

However, the present invention is not limited to the description of the examples, and the presented information reconstructing model generation device 110 may generate the presented information reconstructing model based on the brain activity signal y_estm (estimated value), which is generated by the individual conversion device 107 based on the y_msrd (measured value), the presented information identification code, and the local base image, instead of the y_msrd (measured value) of the target subject in the present embodiment. In this case, the presented information reconstruction device 1122 may reconstruct the presenting information based on the brain activity signal y_estm (estimated value) and generated presented information reconstructing model.

Next, verification results obtained by performing the above-described processing with the brain activity deducing apparatus 1 related to the present embodiment are explained. Number of the subjects was 3 in the verification. Their measured brain signals were acquired from the 3 subjects after obtaining informed consent. When the individual conversion information and the presented information reconstructing model were generated, the images it1 to it4 in FIGS. 6A to 6D or random dot patters similar to these images were presented to the subject to be measured in a random order with the information presentation device 103. This is for activating the entire brain and avoiding the brain activity from being localized to a specific area. For example, the procedure, is performed in order to avoid the brain activity signal corresponding to an image presented on the left side from being unmeasurable or undeducible when an image is presented on the right side only.

During generating the presented information categorizing model and measuring the brain activity signal of the source subject, one of the five still images ip1 to ip5 shown in FIGS. 7A to 7E was presented to the subject to be measured by the information presentation device 103 as a presenting information in a random order. The numbers of the pixels of the presented random dot patterns and the images ip1 to ip5 were 10 pixels horizontally and 10 pixels vertically.

The presenting time of the presenting information was 12 second per image. After presenting the presenting information, break time of 12 second was introduced. In every 12 second presenting time, the brain activity signal was obtained by the brain activity measurement device 101. The voxel number included in the obtained brain activity signal was 1000.

In this verification, by using the brain activity deducing apparatus 1 to each subject to be measured, the brain activity measuring process shown in FIG. 10 and the brain activity deducing process shown in FIG. 11 were performed.

FIG. 13 is a table showing an example indicating the correlation between the brain activity signals related to an embodiment of the present invention.

The upper-most row of FIG. 13 indicates source subjects 1 to 3 in order from the second column to the fourth column. The left-most column of FIG. 13 indicates target subjects 1 to 3 in order from the second row to the fourth row. Each section below the second row and right to the second column in FIG. 13 indicates the average value of the voxel-wise correlation between voxels with standard deviation shown in parentheses. The voxel-wise correlation is the correlation coefficient computed based on the element signal value for each voxel of the target subject deduced by the individual conversion device 107 from the brain activity signal of the source subject, and on the element signal value for each voxel of the target subject obtained by the brain activity measurement device 101.

As shown in FIG. 13, in a case where the source and target subjects were the subject to be measured 1 and 2, respectively, the average value of the voxel-wise correlation was 0.42, and the standard deviation was 0.15. In a case where the source subject was the subject to be measured 1, and the target subject was the subject to be measured 3, the average value of the voxel-wise correlation was 0.19, and the standard deviation was 0.23. In a case where the source subject was the subject to be measured 2, and the target subject was the subject to be measured 1, the average value of the voxel-wise correlation was 0.54, and the standard deviation was 0.12. In a case where the source subject was the subject to be measured 2, and the target subject was the subject to be measured 3, the average value of the voxel-wise correlation was 0.15, and the standard deviation was 0.21. In a case where the source subject was the subject to be measured 3, and the target subject was the subject to be measured 1, the average value of the voxel-wise correlation was 0.49, and the standard deviation was 0.14. In a case where the source subject was the subject to be measured 3, and the target subject was the subject to be measured 2, the average value of the voxel-wise correlation was 0.31, and the standard deviation was 0.18.

When the Wilcoxson signed-rank test, which is one of statistical hypothesis testing, was applied to the above-mentioned results, the p value became less than 0.01. Therefore, the results shown in FIG. 13 indicates that the deduced and measured brain activity signals had a significant-correlation.

FIG. 14 is a table showing an example indicating the percentage of correct answers (accuracy of classification) of the presented information related to an embodiment of the present invention.

The upper-most row in FIG. 14 indicates source subjects 1 to 3 in order from the second column to the fourth column. The left-most column in FIG. 14 indicates the target subjects 1 to 3 in order from the second row to the fourth row. Each section below the second row and right to the second column in FIG. 14 indicates the percentage of the accuracy of classification of the presenting information. In this verification, the percentage of the accuracy of classification is the ratio of the number of correct discrimination made by the presented information categorizing device 1121 using the target subject's brain activity signal, which was deduced from the source subject's brain activity, to the total number of information presentation.

According to the data shown in FIG. 14, in a case where the source subject was the subject 1 and the target subject was the subject 2, the percentage of the accuracy of classification was 84%. In a case where the source subject was the subject 1 and the target subject was the subject 3, the percentage of the accuracy of classification was 49%. In a case where the source subject was the subject 2 and the target subject was the subject 1, the percentage of the accuracy of classification was 87%. In a case where the source subject was the subject 2 and the target subject was the subject 3, the percentage of the accuracy of classification was 62%. In a case where the source subject was the subject 3 and the target subject was the subject 1, the percentage of the accuracy of classification was 86%. In a case where the source subject was the subject 3 and the target subject was the subject 2, the percentage of the accuracy of classification was 82%.

As shown in FIG. 14, in the case where the target subject was the subject 1 or the subject 2, the percentage of the accuracy classification was high, such as higher than 80%. When the target subject was the subject 3, the percentage was relatively low, such as 49% or 62%. However, even in the case with relatively low percentage, it was significantly higher than 20%, which is the percentage of the accuracy classification at a change level.

FIG. 15 is a table showing an example indicating the correlation between the presented information related to an embodiment of the present invention.

The upper-most row in FIG. 15 indicates the source subjects 1 to 3 in order from the second column to the fourth column. The left-most column in FIG. 15 indicates the target subjects 1 to 3 in order from the second row to the fourth row. Each section below the second row and right to the second column in FIG. 15 indicates the average value of the pixel-wise correlation between pixels with standard deviation shown in parentheses. The pixel-wise correlation is the correlation coefficient computed based on the signal value for each pixel of the image signal reconstructed based on the target subject's brain activity deduced by the presented information categorizing device 1121 and on the signal value for each pixel of the presenting information presented by the information presentation device 103.

According to the data shown in FIG. 15, in a case where the source subject was the subject 1 and the target subject was the subject 2, the average value of the pixel-wise correlation was 0.74, and the standard deviation was 0.08. In a case where the source subject was the subject 1 and the target subject was the subject 3, the average value of the pixel-wise correlation was 0.67, and the standard deviation was 0.13. In a case where the source subject was the subject 2 and the target subject was the subject 1, the average value of the pixel-wise correlation was 0.72, and the standard deviation was 0.12. In a case where the source subject was the subject 2 and the target subject was the subject 3, the average value of the pixel-wise correlation was 0.61, and the standard deviation was 0.15. In a case where the source subject was the subject 3 and the target subject was the subject 1, the average value of the pixel-wise correlation was 0.60, and the standard deviation was 0.14. In a case where the source subject was the subject 3 and the target subject was the subject 2, the average value of the pixel-wise correlation was 0.57, and the standard deviation was 0.13.

When the Wilcoxson signed-rank test was applied to the above-mentioned results, the p value became less than 0.01. Therefore, the results shown in FIG. 15 indicates that the deduced and measured brain activity signals had a significant-correlation.

The correlation coefficients indicated in FIG. 15 are generally higher than those indicated in FIG. 13. The reason for this is that bias value was introduced by the brain activity measurement device 101 and the presented information categorizing device 1121 when the contrast value was deduced using the formula (8), and the element signals of brain activity signal with a low relevancy to the presenting information in the sparse regression were removed.

As explained above, the perceptible information is presented to the subject, the brain activity signal representing the brain activity of the subject is obtained, and the individual conversion information representing correlation between the brain activity signal of the first subject and that of the second subject is computed in the present embodiment. Because of this, the individual conversion information, which is needed for deducing the brain activity signal of the target subject who is the second subject, can be obtained without directly measuring it. As a result, according to the present embodiment, the information process using the brain activity signal can be utilized in a wider application range compared to the conventional approach.

Also, according to the present embodiment, the perceptible information is presented to the first subject, the brain activity signal representing the brain activity of the first subject is obtained, and the brain activity of the second subject is deduced from the brain activity signal obtained from the individual conversion information representing correlation between the brain activity signal of the first subject and that of the second subject. Because of this, the brain activity signal of the target subject, who is the second subject, can be deduced without directly measuring it. As a result, according to the present embodiment, the information process using the brain activity signal limited to the target subject can be utilized in a wider application range.

It takes a high cost and a long time for measuring the brain activity signal. However, according to the present embodiment, the brain activity signal of the target subject can be deduced based on the brain activity signal of the source subject. Therefore, comparing to the conventional method, in which the brain activity signal of the target subject is measured one by one, the cost and the time for measurement can be significantly reduced in the present embodiment. In the conventional approach, the subjects to be measured are subjected to a long binding hour (for example, several hours), and psychological and physical burden. However, such burden can be reduced according to the present embodiment.

The above-described brain activity deducing apparatus 1 of the present embodiment can be configured to have two or more brain activity measurement devices 101 and to be able to obtain the brain activity signals from 2 subjects or more at the same time.

A part of the above-described brain activity deducing apparatus 1, for example, the individual conversion variable computation device 105, the individual conversion device 107, the presented information categorizing model generation device 108, the presented information reconstructing model generation device 110, the noise removal device 114, the presented information categorizing device 1121, or the presented information reconstruction device 1122 can be handled by a computer. In such a case, a program for achieving the controlling function may be stored in a storage media readable by the computer, the stored program may be read out by the computer system, and the read out program may be executed. Here, "the computer system" means a computer system installed on the brain activity deducing apparatus 1, and includes an OS and hardware such as a peripheral device or the like. Also, "the storage media readable by the computer" means a transportable media, such as a flexible disk, a magneto optical disk, ROM, CD-ROM, or the like, and a storage device provided in the computer system, such as a hard drive or the like. Also, "the storage media readable by the computer" may include what retains the program dynamically in a short period of time, such as a communication wire used in transmitting the program through a network, such as the internet, or a communication line, such as a phone line, and what retains the program temporally, such as a volatile memory in a computer system in a server or a client in the network. Also, the above-described program may be for achieving a portion of the functions described above. Also, the part of the above-described function may be achieved by combining the above-described function and a program already stored in the computer system.

Also, a part or all of the above-described brain activity deducing apparatus 1 of the present embodiment may be achieved as an integrated circuit of an LSI (Large Scale Integration) or the like.

Each functional block of the brain activity deducing apparatus 1 may be turned in a processor individually. Also, a part or all of the each functional block may be turned into a processor by integration. The method for integration is not limited to the LSI, and a dedicated circuit or a multi-purpose processor may be used. Also, if a technology for integrating circuit substituting the LSI is available because of technical advancement, an integrated circuit using such a technology may be used.

The brain activity deducing apparatus 1 of the present embodiment can be utilized to a brain-machine interface (BMI) by deducing the brain activity signal of an user based on the individual conversion information and converting the deduced brain activity signal to a controlling signal for controlling an external device. In the configuration described above, the brain activity measuring time for constructing a decode model for a specific user can be shorted by using the deduced brain activity data, and a BMI apparatus with less burden on the users can be obtained.

Also, a brain activity database can be constructed by converting brain activity signal data of numbers of users, who a variety of presenting information are presented to, into brain activity signal data of a specific person, and storing the converted data. By having the configuration described above, A large scale database of brain activity data can be constructed, suppressing the volume of data at the same time, by storing individual conversion information for a such conversion and the brain activity signals of the specific person as a database.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A brain activity measuring apparatus comprising:
an information presentation device that presents perceptible information to a first subject and a second subject;
a brain activity measurement device that acquires a brain activity signal representing a brain activity of the first subject and a brain activity signal representing a brain activity of the second subject; and
an individual conversion information computation device that computes an individual conversion information, which correlates the brain activity signal of the first subject and the brain activity signal of the second subject.

2. The brain activity measuring apparatus according to claim 1, wherein
the brain activity measurement device resolves the acquired brain activity signals into element signals;
element signal intensities of the brain activity signals are information indicating brain activity levels per voxel in a cephalic part of the first subject or the second subject; and
the individual conversion information computation device computes, as the individual conversion information, correlation coefficients each of which correlates an element signal of an i-th voxel of the first subject and an element signal of a j-th voxel of the second subject by using the hierarchical Baysian estimation.

3. The brain activity measuring apparatus according to claim 2, wherein
the individual conversion information computation device sets a weight corresponding to one of the correlation coefficients to 0 during computing the individual conversion information by an iterative operation for the hierarchical Baysian estimation, in a case where correlation between the element signal of the i-th voxel of the first subject and the element signal of the j-th voxel of the second subject is determined to be low based on a predetermined threshold value.

4. The brain activity measuring apparatus according to claim 3, further comprising an individual conversion information memory device that stores the individual conversion information for each pair of subjects including the first subject and the second subject.

5. The brain activity measuring apparatus according to claim 4, further comprising an individual conversion device that deduces the brain activity of the second subject from the brain activity of the first subject measured with the brain activity measurement device based on the correlation coefficient stored in the individual conversion information memory device.

6. A brain activity measuring method in which a brain activity of a subject is measured with a brain activity measuring apparatus comprising:
a first step of presenting, by the brain activity measuring apparatus, perceptible information to a first subject and a second subject;
a second step of acquiring, by the brain activity measuring apparatus, a brain activity signal representing a brain activity of the first subject and a brain activity signal representing a brain activity of the second subject; and
a computing step of computing, by the brain activity measuring apparatus, an individual conversion information which correlates the brain activity signal of the first subject and the brain activity signal of the second subject.

7. A brain activity deducing apparatus comprising:
an information presentation device that presents perceptible information to a first subject;
a brain activity measurement device that acquires a brain activity signal representing a brain activity of the first subject; and
an individual conversion device that deduces a brain activity signal of a second subject from the acquired brain activity signal of the first subject based on an individual conversion information, which correlates a pre-acquired brain activity signal of the first subject and a pre-acquired brain activity signal of the second subject.

8. The brain activity deducing apparatus according to claim 7, further comprising a reconstructed model generation device generating a reconstructed model of a presented information, wherein
the reconstructed model generation device outputs an image signal, which represents a 1-frame image corresponding to the presented information, from the deduced brain activity signal of the second subject as a linear combination of respective products of local basal images and deduced contrast values.

9. A brain activity deducing method in which a brain activity of a subject is deduced with a brain activity deducing apparatus comprising the steps of:
presenting perceptible information to a first subject with the brain activity deducing apparatus;

acquiring a brain activity signal representing a brain activity of the first subject with the brain activity deducing apparatus; and deducing a brain activity signal of a second subject from the acquired brain activity signal of the first subject based on an individual conversion information with the brain activity deducing apparatus, wherein the brain activity deducing device comprises an individual conversion information memory device that stores the individual conversion information, which correlates a pre-acquired brain activity signal of the first subject and a pre-acquired brain activity signal of the second subject.

10. A brain-machine interface device comprising:

an information presentation device that presents perceptible information to a first subject;

a brain activity measurement device that acquires a brain activity signal representing a brain activity of the first subject;

an individual conversion device that deduces a brain activity signal of a second subject from the acquired brain activity signal of the first subject based on an individual conversion information, which correlates a pre-acquired brain activity signal of the first subject and a pre-acquired brain activity signal of the second subject; and a control signal conversion device that converts the brain activity signal of the second subject deduced with the individual conversion device to a control signal controlling an external device.

* * * * *